United States Patent
McClung et al.

(10) Patent No.: US 11,464,426 B2
(45) Date of Patent: Oct. 11, 2022

(54) PASSIVE, PROPORTIONAL MEASUREMENT OF OXYGEN AND CARBON DIOXIDE CONSUMPTION FOR ASSESSMENT OF METABOLIC PARAMETERS

(71) Applicant: Massachusetts Institute of Technology, Cambridge, MA (US)

(72) Inventors: Holly McClung, Westborough, MA (US); Reed Wasson Hoyt, Cambridge, MA (US); Lawrence M Candell, Arlington, MA (US); Joseph M. Mahan, Beverly, MA (US); Gary A Shaw, Westford, MA (US); Andrew M Siegel, Arlington, MA (US); Robert Linton Standley, Acton, MA (US); Kyle Thompson, Lynnfield, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 672 days.

(21) Appl. No.: 16/414,003

(22) Filed: May 16, 2019

(65) Prior Publication Data
US 2020/0022618 A1 Jan. 23, 2020

Related U.S. Application Data

(60) Provisional application No. 62/672,443, filed on May 16, 2018.

(51) Int. Cl.
*A61B 5/097* (2006.01)
*A61B 5/083* (2006.01)
(Continued)

(52) U.S. Cl.
CPC .............. *A61B 5/097* (2013.01); *A61B 5/087* (2013.01); *A61B 5/0833* (2013.01);
(Continued)

(58) Field of Classification Search
None
See application file for complete search history.

(56) References Cited

U.S. PATENT DOCUMENTS

| | | |
|---|---|---|
| 1,329,559 A | 2/1920 | Nikola |
| 2,630,798 A | 3/1953 | White et al. |
| | (Continued) | |

FOREIGN PATENT DOCUMENTS

| | | |
|---|---|---|
| WO | 2014116604 A1 | 7/2014 |
| WO | 2015011714 A1 | 1/2015 |

OTHER PUBLICATIONS https://news.mit.edu/2017/monitoring-metabolic-energy-expenditure-health-fitness-with-breath-analyzer-0727 Monitoring metabolic energy expenditure, health, and fitness with a breath analyzer, Erin LEE (Year: 2017).*

(Continued)

*Primary Examiner* — Jay B Shah
(74) *Attorney, Agent, or Firm* — Smith Baluch LLP

(57) ABSTRACT

A conventional flow tube for a metabolic cart is usually a straight length of pipe whose inner diameter is fixed by the respiratory burden imposed by the flow tube on the user, with a smaller diameter imposing a higher respiratory burden. The ratio of the straight flow tube's length to diameter is fixed by fluid dynamics, so increasing the flow tube's diameter causes the flow tube's length to increase. As the flow tube gets longer, it exerts more torque on the user's neck and jaw, creating discomfort. Reducing the flow tube's length causes an undesired increase in the respiratory burden but increasing the flow tube's diameter to reduce the respiratory burden makes the flow tube less comfortable, making the flow tube unconformable, hard to breathe through, or both. Bending the flow tube, e.g., in an L shape, makes it (Continued)

possible to increase the flow tube's propagation length without increasing the flow tube's lever arm length.

22 Claims, 34 Drawing Sheets

(51) Int. Cl.
    *A61B 5/087*     (2006.01)
    *A61M 16/08*     (2006.01)

(52) U.S. Cl.
    CPC ........ *A61B 5/0836* (2013.01); *A61B 2562/06* (2013.01); *A61M 16/0808* (2013.01)

(56) References Cited

U.S. PATENT DOCUMENTS

| | | | |
|---|---|---|---|
| 5,042,501 | A | 8/1991 | Kenny et al. |
| 5,072,737 | A | 12/1991 | Goulding |
| 5,363,857 | A | 11/1994 | Howard |
| 5,555,890 | A | 9/1996 | Schaller |
| 6,884,222 | B1 | 4/2005 | Braig |
| 6,969,357 | B1 | 11/2005 | Colman et al. |
| 7,621,271 | B2 | 11/2009 | Brugnoli |
| 8,197,417 | B2 | 6/2012 | Howard et al. |
| 10,638,956 | B2 | 5/2020 | Candell et al. |
| 11,259,717 | B2 | 3/2022 | Thompson et al. |
| 2002/0017467 | A1 | 2/2002 | Ando et al. |
| 2002/0162397 | A1 | 11/2002 | Orr et al. |
| 2003/0050567 | A1 | 3/2003 | Baghdassarian |
| 2004/0094155 | A1 | 5/2004 | Castor et al. |
| 2004/0162500 | A1 | 8/2004 | Kline |
| 2004/0176698 | A1 | 9/2004 | Robergs et al. |
| 2004/0186389 | A1 | 9/2004 | Mault et al. |
| 2004/0249300 | A1 | 12/2004 | Miller |
| 2006/0201503 | A1 | 9/2006 | Breen |
| 2006/0229526 | A1 | 10/2006 | Chen et al. |
| 2008/0289628 | A1 | 11/2008 | Hallback et al. |
| 2009/0056409 | A1 | 3/2009 | Howard et al. |
| 2009/0227887 | A1 | 9/2009 | Howard et al. |
| 2009/0299208 | A1 | 12/2009 | Takahashi et al. |
| 2010/0036266 | A1 | 2/2010 | Myklebust et al. |
| 2010/0185112 | A1 | 7/2010 | Kesteren et al. |
| 2010/0249634 | A1 | 9/2010 | Hansen |
| 2010/0313963 | A1 | 12/2010 | Skinn |
| 2011/0009764 | A1 | 1/2011 | Lanier et al. |
| 2012/0029321 | A1 | 2/2012 | Makaretz et al. |
| 2012/0125335 | A1 | 5/2012 | Affinito |
| 2012/0130698 | A1 | 5/2012 | Kovatchev et al. |
| 2012/0272961 | A1 | 11/2012 | Masic et al. |
| 2014/0128691 | A1 | 5/2014 | Olivier |
| 2014/0194703 | A1 | 7/2014 | Wondka et al. |
| 2014/0235961 | A1 | 8/2014 | Brugnoli |
| 2015/0032019 | A1 | 1/2015 | Acker et al. |
| 2015/0033824 | A1 | 2/2015 | Hammarlund et al. |
| 2015/0065900 | A1 | 3/2015 | Wondka et al. |
| 2015/0114395 | A1 | 4/2015 | Heinonen et al. |
| 2015/0177103 | A1 | 6/2015 | Brown et al. |
| 2016/0100774 | A1 | 4/2016 | Wilcox et al. |
| 2016/0166175 | A1 | 6/2016 | Mor et al. |
| 2016/0220147 | A1 | 8/2016 | Mor et al. |
| 2017/0055875 | A1 | 3/2017 | Candell et al. |
| 2018/0125391 | A1 | 5/2018 | Candell et al. |

OTHER PUBLICATIONS

Acheson, K. J. et al., "Glycogen storage capacity and de novo lipogenesis during massive carbohydrate overfeeding in man," Am. J. Clin. Nutrit., 48, pp. 240-247 (1988).

Bouchard, C. et al., "The Response to Exercise with Constant Energy Intake in Identical Twins," Obesity Research, 2(5), pp. 400-410 (Sep. 1994).

Cruickshank, E. W. H. et al., "The Respiratory Quotient, Oxygen Consumption and Glycogen Content of the Mammalian heart in Aglycaemia," J. Physiol., 80(2), pp. 179-192 (1933).

Extended European Search Report in European Patent Application No. 16831300.5 dated Feb. 19, 2019, 11 pages.

Fink et al., "Problems with inhaler use: a call for improved clinician and patient education." Respiratory care 50.10 (2005): 1360-1375.

Ganz, M. L. et al., "The association of body mass index with the risk of type 2 diabetes: a case-control study nested in an electronic health records system in the United States," Diabetology & Metabolic Syndrome, 6(50), pp. 1-8 (2014).

Guh, D. P. et al., "The incidence of co-morbidities related to obesity and overweight: A systematic review and meta-analysis," BMC Public Health, 9(88), pp. 1-20 (2009).

Hall, "Estimating human energy intake using mathematical models," American Journal of Clinical Nutrition, 2014;100:744-5.

Hargrove, J. L., "History of the Calorie in Nutrition," The Journal of Nutrition, 136(12), pp. 2957-2961 (2006).

International Search Report and Written Opinion in International Patent Application No. PCT/US19/32610 dated Jul. 23, 2019, 12 pages.

International Search Report and Written Opinion in International Patent Application No. PCT/US19/32611 dated Jul. 29, 2019, 9 pages.

International Search Report and Written Opinion dated Dec. 30, 2016 for International Application No. PCT/US16/44288, 13 pages.

Jebb, S. A. et al., "In vivo measurement of changes in body composition: description of methods and their validation against 12-d continuous whole-body calorimetry," Am. J. Clin. Nutrit. 58, pp. 455-462 (1993).

Ladenheim, E. E., "Liraglutide and obesity: a review of the data so far," Drug Design, Development and Therapy, 9, pp. 1867-1875 (2015).

Levi et al., "F as in fat: how obesity threatens America's future 2012." (2012). 116 pages.

Ludwig, D. S. et al., "Increasing Adiposity. Consequence or Cause of Overeating?," JAMA, 311(21), pp. 2167-2168 (Jun. 2014).

MacFarlane et al., "Inter-unit variability in two ParvoMedics TrueOne 2400 automated metabolic gas analysis systems." European journal of applied physiology 113.3 (2013): 753-762.

McDevitt, R. M. et al., "De novo lipogenesis during controlled overfeeding with sucrose or glucose in lean and obese women," Am. J. Clin. Nutrition, 74(6), pp. 737-746 (2001).

Mozaffarian, D. et al., "Changes in Diet and Lifestyle and Long-Term Weight Gain in Women and Men," The New England Journal of Medicine, 364(25), pp. 2392-2404 (Jun. 2011).

Phillips et al., "Short-term intra-subject variation in exhaled volatile organic compounds (VOCs) in COPD patients and healthy controls and its effect on disease classification." Metabolites 4.2 (2014): 300-318.

Reeves et al., "Reducing the time period of steady state does not affect the accuracy of energy expenditure measurements by indirect calorimetry." Journal of applied physiology 97.1 (2004): 130-134.

Sethi et al., "Clinical application of volatile organic compound analysis for detecting infectious diseases." Clinical microbiology reviews 26.3 (2013): 462-475.

Siekmeier et al., "Systemic treatment by inhalation of macromolecules-principles, problems, and examples." J Physiol Pharmacol 59.Suppl 6 (2008): 53-79.

Weiss, R. et al., "Obesity and the Metabolic Syndrome in Children and Adolescents," The New England Journal of Medicine, 350(23), pp. 2362-2374 (Jun. 2003).

\* cited by examiner

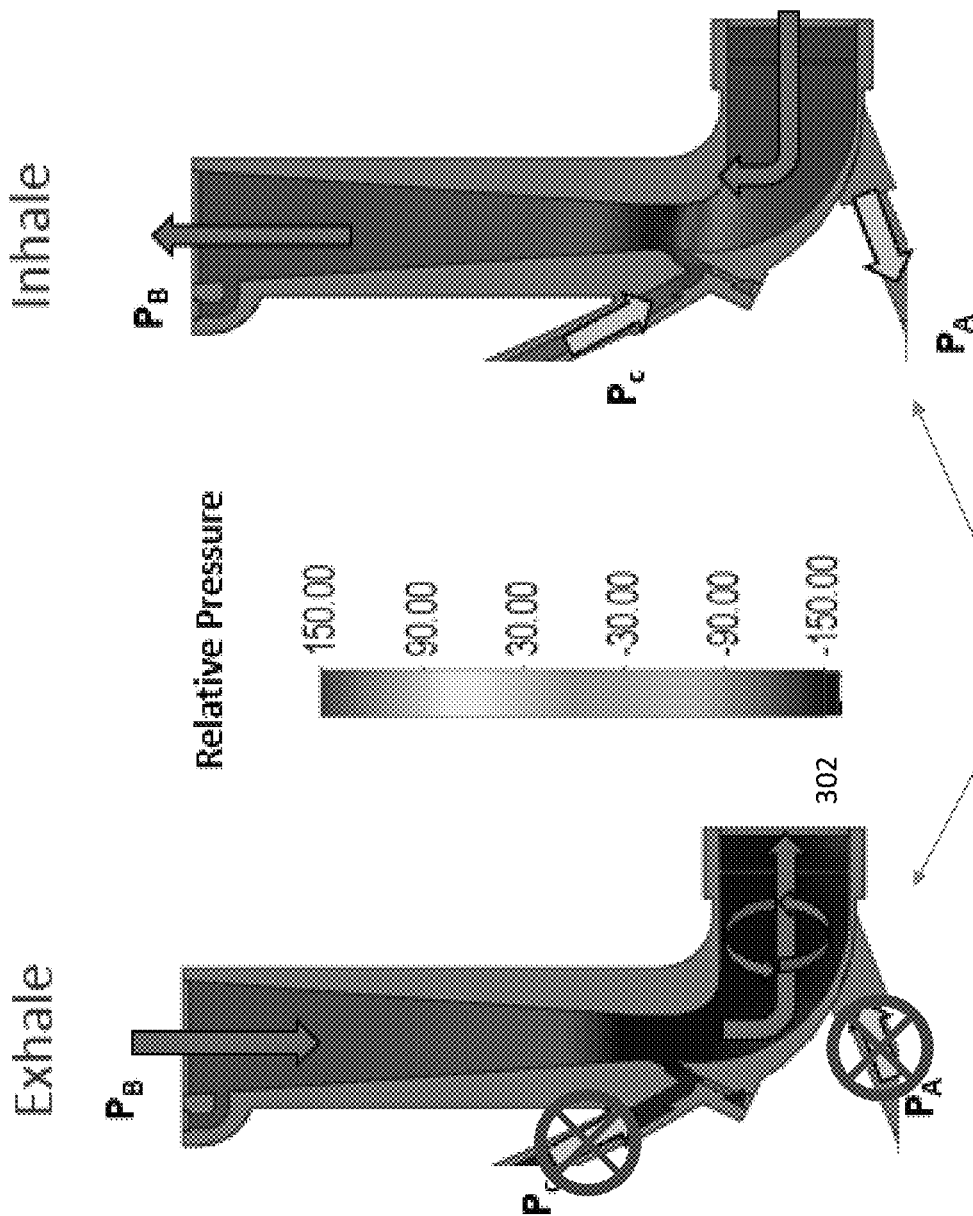

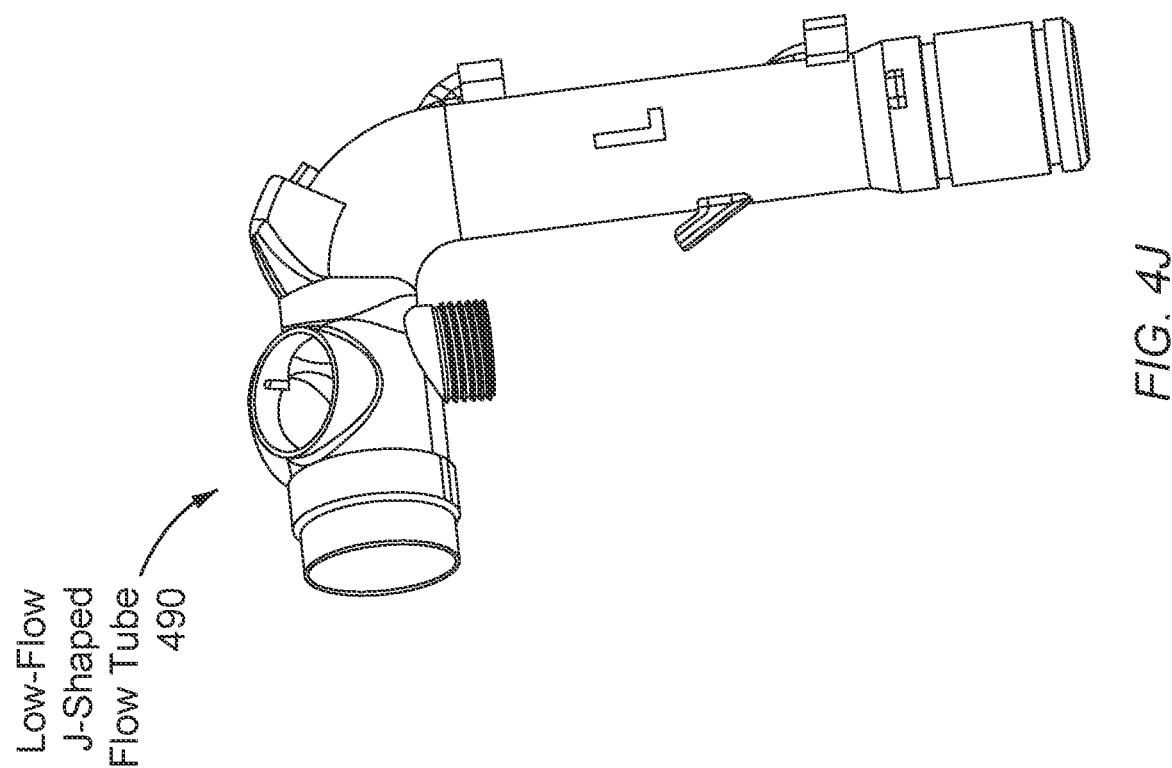

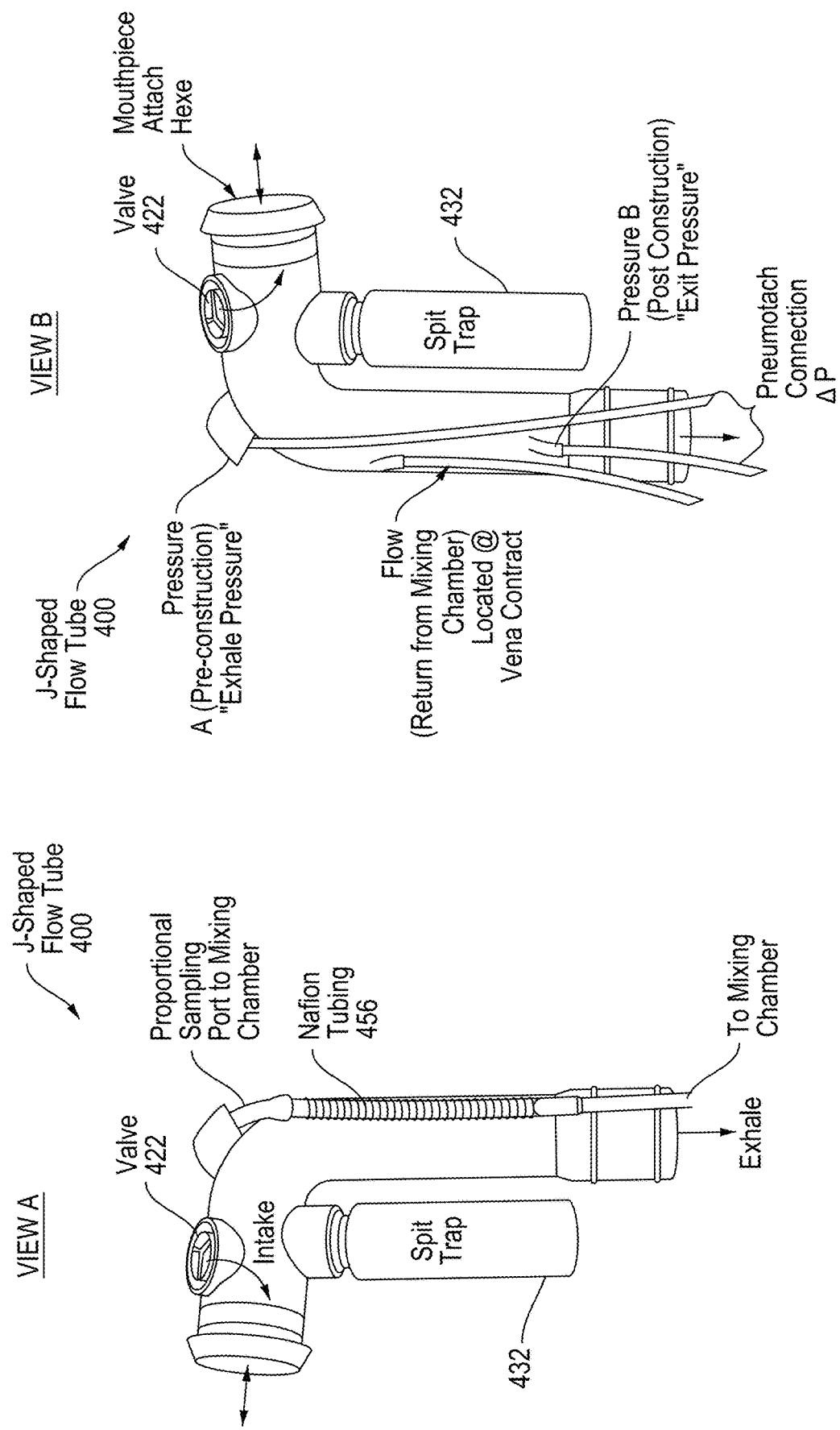

Fig 8. This shows the pressure contours in color. High pressure on the outside and low pressure on the inside for flow through a 90 deg bend and the arrows are the velocity vectors.

| Description | Characteristics |
|---|---|
| 1. Unstalled 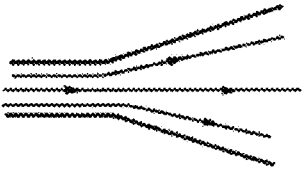 | Flow follows diffuser contours.<br>Flow is steady. |
| 2. Appreciable Stall 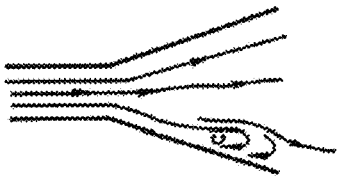 | Flow generally follows diffuser contours. Boundary layers thicken. Small regions of separation and erratic flow are generally first seen in corners and they occupy no more than 1/5 of diffuser wall. There is little or no reverse flow. |
| 3. Large Transitory Stall 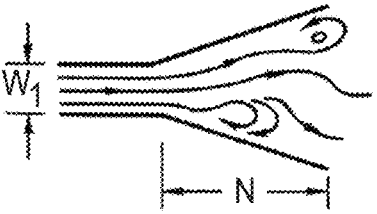 | Flow is erratic with gross oscillation of pressure and overall flow pattern. Stalled regions with reverse flow form and then wash out.<br>$N/W_1 < 4$: stalls occur on 1 diverging wall.<br>$4 < N/W_1 < 12$: stalls occur on both diverging walls (shown).<br>$N/W_1 > 16$: stalls occur on parallel walls. |
| 4. Fully Developed Stall  | Flow separates near throat and forms a large, stable, fixed eddy along one diverging wall while the flow follows second diverging wall. Near-steady flow with reverse flow in eddy. Eddy can be moved from one wall to the other wall only by large disturbances. |
| 5. Jet Flow 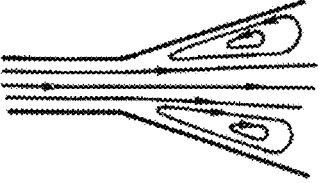 | Incoming flow separates from both diffuser walls near throat and proceeds as a jet down diffuser. Large fixed eddies form on diverging wall. Flow is steady with substantial regions of reverse flow. Diffuser pressure recovery is very poor. |

FIG. 12

PASSIVE, PROPORTIONAL MEASUREMENT OF OXYGEN AND CARBON DIOXIDE CONSUMPTION FOR ASSESSMENT OF METABOLIC PARAMETERS

CROSS-REFERENCE TO RELATED APPLICATIONS

This application claims the priority benefit, under 35 U.S.C. 119(e), of U.S. Application No. 62/672,443, filed May 16, 2018, and entitled "A System for Passive, Proportional Measurement of Oxygen and Carbon Dioxide Consumption for Assessment of Metabolic Parameters," which is incorporated by reference herein in its entirety.

This application is related to concurrently filed U.S. application Ser. No. 16/413,980, entitled "Methods and Apparatus for Passive, Proportional, Valveless Gas Sampling and Delivery," which claims the priority benefit, under 35 U.S.C. 119(e), of U.S. Application No. 62/672,440, filed May 16, 2018, and entitled "Methods and Apparatus for Passive, Proportional, Valveless Gas Sampling and Delivery." Each of these applications is incorporated by reference herein in its entirety.

GOVERNMENT SUPPORT

This invention was made with Government support under Grant No. FA8702-15-D-0001 awarded by the U.S. Air Force. The Government has certain rights in the invention.

BACKGROUND

Indirect calorimetry is a well-established methodology by which in vivo gas exchange measurements, volume of oxygen consumed ($VO_2$), and volume of carbon dioxide ($VCO_2$) exhaled by an individual are used to estimate the rate of substrate utilization and energy metabolism (expenditure). Metabolic energy expenditure by an individual performing a specific activity results in heat production and may also result in useful mechanical work (e.g., when lifting a mass against the force of gravity from a given height to a greater height). Metabolic energy expenditure during a given activity can be accurately estimated from $VO_2$ and the respiratory exchange ratio (RER) (i.e., the ratio of $VCO_2$ to $VO_2$). The RER reflects the macronutrients being oxidized (predominantly carbohydrates and/or fats). The RER, along with the volume rate of oxygen consumed, allows estimation of the energy expenditure and the macronutrients (fuel substrates) being oxidized to providing metabolic energy. The volume rates of oxygen consumption and carbon dioxide production can be determined non-invasively by constituent gas and volume flow rate analysis of exhaled breath.

The science of indirect calorimetry was introduced over 100 years ago and exploits the stoichiometry of metabolic chemical reactions to determine which and how many of the reactions are occurring. At the turn of the $20^{th}$ century, state of the art measurements required a trained physiologist to carry a large receptacle, typically a leak-proof bag, and stand or travel alongside a subject to collect exhaled breath and record the elapsed time for the breath collection. Following the collection, the breath is analyzed to determine both the gas volume exhaled per unit time and the oxygen and carbon dioxide concentrations. These measurements are combined to quantify (calculate) the subject's average energy expenditure during the period(s) over which the breath samples were collected. This process is called the Douglas bag technique after its inventor, Gordon Douglas, and is still used as a gold standard.

Today, applications of indirect calorimetry generally fall into one of three architectural classes: whole room, mixing chamber, and breath-by-breath devices. Each of these systems is designed to address a unique experimental need, resulting in different constraints, performance, and costs. Indirect calorimetry is typically used to determine the energy expenditure associated with different physical activities (rest to vigorous activity) and/or the macronutrients oxidized to provide providing metabolic energy during those activities.

The largest and most costly indirect calorimetry system is the whole room calorimeter. In this approach, the participant is confined to a controlled space, typically a small 'room' just large enough for the calorimetry equipment and with precise monitoring of the incoming and outgoing gas composition and volume rate. Highly sensitive mass spectrometers are used to measure the small changes in the gas composition entering and leaving the room as the participant performs various activities as directed. The principle advantage of this approach is allowing metabolic fuel measurements to be made under relatively unconstrained free-living conditions, where the participant is not tethered to a machine or required to breathe directly into a face mask or mouthpiece, all of which can limit or impact performance of activities. Whole room calorimeters are suitable for conducting long-duration experiments, extending over days or weeks, and collecting data over a variety of activities from sleep to high intensity exercise.

However, there are limitations to the types of activities that can be conducted in a closed room system, such as a whole room calorimeter. For investigations of acute athletic performance or situational energy expenditure during specified activities, other approaches are better suited. Another disadvantage of a whole room calorimeter is coarse temporal resolution. A single exhaled breath may have a volume of a liter, whereas a whole room calorimeter designed to support a range of activities may have a volume of 20,000 liters or more. As a consequence, the time for exhaled breath to diffuse into the room and impact the gas concentration as the air exits the room may be many minutes or hours, depending on the size of the room.

A second class of metabolic fuel sensor, the mixing chamber, often referred to as a metabolic cart, evolved from the Douglas bag approach. Mixing chamber approaches have become the standard for laboratory and clinical measurements because they achieve relatively high temporal resolution and accuracy at much lower cost and ease of use than whole-room indirect calorimetry. In the mixing chamber approach, participants breathe directly into a facemask or specially designed mouthpiece equipped with a set of one-way check valves to control the gas flow direction and ensure that only the exhaled breath is collected for subsequent analysis. Unlike the sealed Douglas bag, the mixing chamber design allows a portion of the expired breath contained in the mixing chamber to be ejected from the rear of the chamber in response to each new breath. However, before a given breath is pushed out of the mixing chamber by subsequent breaths, it passes through a series of baffles that mix each incoming breath with the residual from previous breaths, forming an analog volumetric average of the previous few exhaled breaths. Therefore, the exhaled breath mixture in the chamber at any time is a composite of a number of previous breaths and represents a moving metabolic average. Since the chamber is only large enough to hold a few complete breaths, the temporal resolution is much higher than a whole room calorimeter.

FIG. 1A is a schematic of a unidirectional check valve assembly 100. It shows the flow path to allow ambient air to flow into the user's respiratory system from while diverting exhaled air via a third port 106 to a mixing chamber (not shown). The unidirectional check valve assembly 100 includes a unidirectional, normally-closed intake check valve 102 that opens on inhalation to allow ambient air into the "T" on its path to the user via port 104. While this intake valve 102 is open, an exit check valve 106 is closed. At the completion of the inhale cycle, the respiratory flow reverses direction, opening the exit check valve 106, which directs the bolus of exhaled gas into the measurement instrument while the intake check valve 102 is closed. After the exhaled breath has been transferred to the measurement device, the user inhales, reversing the flow direction and again opening intake input check valve 102 and repeating the cycle. The check valves 102 and 106 allow inhalation of ambient air and capture of exhaled breath for analysis while preventing the incursion of ambient air into the measurement device and preventing loss of exhaled breath to the atmosphere during the breathing cycle. These valves 102 and 106, however, represent a respiratory burden to the user and require finite amounts of pressure to open. The volume of the T connector also acts as a reservoir for a portion of the end tidal exhalation, which effectively increases the respiratory system's dead space and results in a bolus of unanalyzed breath.

FIG. 1B shows how the check valve assembly 100 of FIG. 1A is connected to a breathing tube 156 and a mixing chamber 160 for a typical metabolic cart. (The check valve assembly in FIG. 1B is flipped about the stem of the "T" with respect to FIG. 1A.) The user breathes out into the check valve assembly 100 via a mouthpiece 152. After the air exits the check valve assembly 100 via the exhale check valve 106 (FIG. 1A), it enters a conduit (breathing tube 156) that transfers the exhaled breath to the gas mixing chamber 160 of the metabolic cart. The breathing tube 156 is connective plumbing between the user and the instrument. A flow meter 158 at the entrance to the mixing chamber 160 measures the total volume of the breath. Once the gas enters the mixing chamber 160, it is allowed to mix with previous breaths to form a volumetric average of the last few breathing cycles, before exiting the port at the back of the mixing chamber. It is the averaged breath in this chamber 160 that is sampled by a constant rate pump and delivered to O2 and CO2 gas analysis sensors in an analysis chamber 164 coupled to the mixing chamber 160 via a drying line 162. Inside the analysis chamber 164, the gas constituents are determined and associated with the measured flow data to provide the $VO_2$ and $VCO_2$ values used to computing the desired metabolic information.

For metabolic carts, the mixing chamber is a key component and serves two purposes; first, it is of sufficient volume to capture and mix multiple breaths to provide a running metabolic average, and second, it holds and isolates the collected breath from the environment, allowing it to be sampled and analyzed in a controlled fashion. The continuous sampling of gas from the mixing chamber and the displacement of gas with each new exhale differentiates the modern metabolic cart from its historical Douglas bag predecessor, which held all of the exhaled breath in a sealed bag, to be analyzed after collection and thus provided only average values over the time of collection. In addition to gas concentration measurements, calculation of energy expenditure requires the volume of the exhaled gas. The combination of the measured exhaled volume, the inhaled gas composition (ambient air), and exhaled gas concentration provide all the information needed for indirect calorimetry calculations.

While much smaller and less costly than whole room calorimeters, the overall weight and volume of metabolic cart systems makes them impractical for ad libitum measurements and field studies. Specifically, a metabolic cart mixing chamber has a typical volume of 3-4 L. With supporting gas sensors, flow sensor, processor, and display, the system volume reaches more than 6 L and total weight increases enough to make the system impractical for mobile use. Consequently, subject testing with metabolic carts is typically conducted by trained operator and constrained to a treadmill, stationary bicycle, or rowing machine in a clinical setting or laboratory environment.

The standard approach to create mobile systems for use in arbitrary environments is the so-called breath-by-breath method. To achieve the small size necessary for mobile use, breath-by-breath systems operate on a different principle than the previously described metabolic carts and whole room calorimeters. These systems employ an "on the fly" measurement technique to avoid the requirement for a large mixing chamber capable of capturing and holding several breaths for measurement. To eliminate the mixing chamber, breath-by-breath systems typically make measurements of flow rates and gas concentrations every 10-20 milliseconds (ms).

Rapid measurement of gas and volume allows the software to effectively carve up each breath into differential volume elements of about 10 to 20 ms in duration. The volume rate of each breath sample is typically measured at 50 Hz to 100 Hz by a spirometer near the mouth, while a pump continuously removes a small percentage of the gas from the inhale and exhale stream at a constant pump rate independent of the instantaneous flow rate of the exhale or inhale breath. Once pumped, the gas sample is passed through a flexible tube to fast-acting, series-connected O2 and CO2 gas concentration sensors. The sequential, rapidly measured gas concentrations are then temporally aligned with the volumetric flow measurements to form the differential volume elements of O2 and CO2 for each time interval. The differential volume elements are integrated together to produce a breath profile with a high temporal resolution, hence the name breath-by-breath system.

FIG. 2 shows a breath-by-breath collection device 200. In FIG. 2, the breathing is conducted through a facemask 206 that measures the volume flow rate of the breath by the spirometer exit port 202. Inside the breathing mask 206, and before the spirometer 202, a pumping line 204 removes a small continuous sample of gas and transports the sample to a sensor suite 210. Inside the sensor suite 210, a pump 216 pulls the breath through an oxygen sensor 212 and carbon dioxide sensor 214 and deposits it back into the ambient environment.

For intra-breath dynamics and rapid metabolic changes, such as adjusting to a changing physical workload, breath-by-breath systems provide the highest temporal resolution and mobility. Since the systems don't require a mixing chamber, they can be made sufficient small to be directly mounted on the subject and powered by a battery to enable mobile measurements of running, rowing, cycling, or energy demands of a variety of athletic and work-related activities.

However, a major challenge for breath-by-breath systems is ensuring accurate time alignment between the flow and gas measurements when each sensor is physically located in a different place and may exhibit different measurement time constants. The alignment of all of these signals is sensitive to the arrangement of the device on the individual, the pump speed, calibration procedure, and the time constants and structure of the individual sensors.

SUMMARY

Inventive calorimeters are small, inexpensive, and simple to use. When an expired gas flow is applied to one side of an inventive calorimeter, a fraction of the flow that is proportional to the instantaneous flow rate of the exhalation is diverted and passed to an exterior measurement chamber before cycling back and joining the main flow path. Unlike other calorimeters, inventive calorimeters perform this flow-rate-proportional sampling without valves or other moving parts. As gas flow is applied in the other (inhale) direction, a fluid dynamic stall is developed across the same gas sampling ports, effectively shutting off flow to the measurement chamber, thus avoiding dilution of the exhale sample by ambient air. This device can be used to collect a representative sample of respired breath with little to no inclusion of diluting ambient gas.

An example of an inventive calorimeter is a flow-rate proportional passive side-stream sampling system with a bent flow tube, a mixing chamber, and at least one sensor. In operation, the bent flow tube receives an exhaled breath from a person. The mixing chamber, which is in fluid communication with a first port between an inlet of the bent flow tube and an outlet of the bent flow tube, receives a fraction of the exhaled breath collected in proportion to an instantaneous flow rate of the exhaled breath. And the sensor, which is in fluid communication with gas in the mixing chamber, measures at least one of a volumetric flow rate, an oxygen content, a carbon dioxide content, an oxygen partial pressure, or a carbon dioxide partial pressure of the fraction of the exhaled breath.

The bent flow tube may have a curve of about 75 degrees to about 105 degrees between the inlet and the outlet. It may define an inner lumen extending from the proximal end to the distal end to convey the exhaled breath from the proximal end to the distal end, with the first port being disposed between the bend and the outlet. The bent flow tube can have a second port disposed between the inlet and the bend. It may also have: at least one valve, disposed between the inlet and the bend and in fluid communication with the inner lumen, to relieve pressure in the inner lumen during an inhalation by the person; a saliva trap, disposed in fluid communication with the inner lumen, to collect saliva excreted by the person; and/or a removable mouthpiece connected to the inlet of the bent flow tube.

The mixing chamber may include a perforated baffle and/or a perforated circuit board disposed between the inlet and the at least one sensor to foster mixing of multiple breath fractions. The sensor can be disposed in the mixing chamber.

Another inventive aspect is a flow tube for a metabolic cart. This flow tube has a proximal end to receive an exhalation from a person, a distal end, and a bend between the proximal end and the distal end. It defines an inner lumen extending from the proximal end to the distal end to convey the exhalation from the proximal end to the distal end. It has a first port between the proximal end and the bend and a second port between the bend and the distal end to convey a portion of the exhalation to a mixing chamber in fluid communication with the lumen. The bend can be about 75 degrees to about 105 degrees (e.g., about 90 degrees).

The flow tube may also have: at least one valve, disposed between the proximal end and the bend and in fluid communication with the lumen, to relieve pressure in the lumen during an inhalation by the person; a saliva trap, disposed in fluid communication with the lumen, to trap saliva excreted by the person; and/or a removable mouthpiece inserted into the proximal end.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

Figures 3A, 3B:
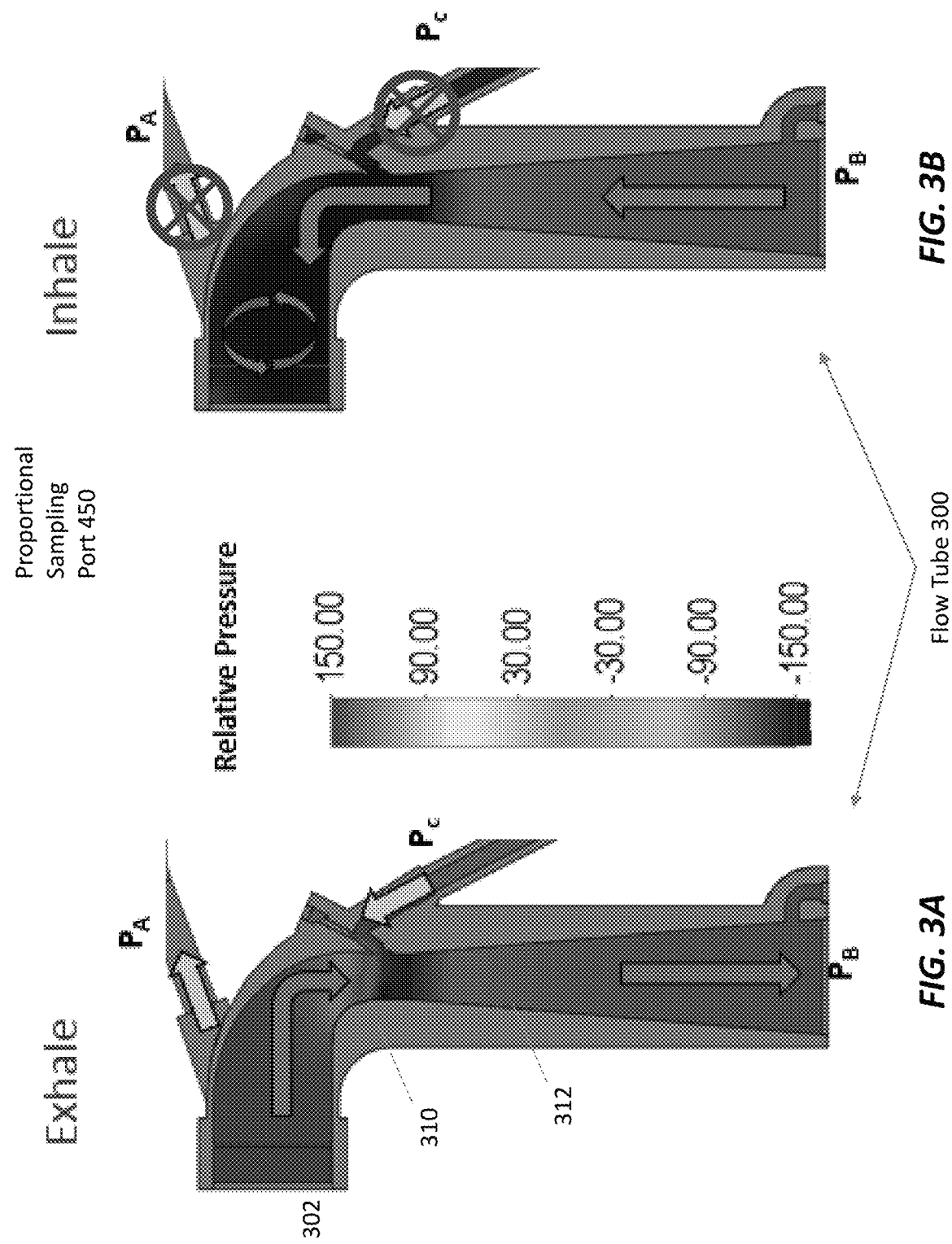
FIGS. 3A and 3B show an inventive flow tube, also called a flow diode, that samples exhalation (FIG. 3A) but not inhalation (FIG. 3B).
Figure 3C:
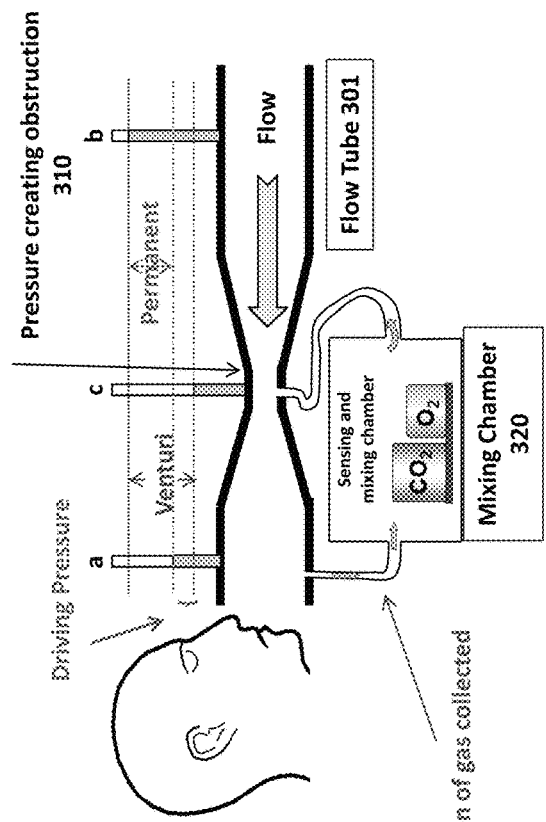
Figure 3D:
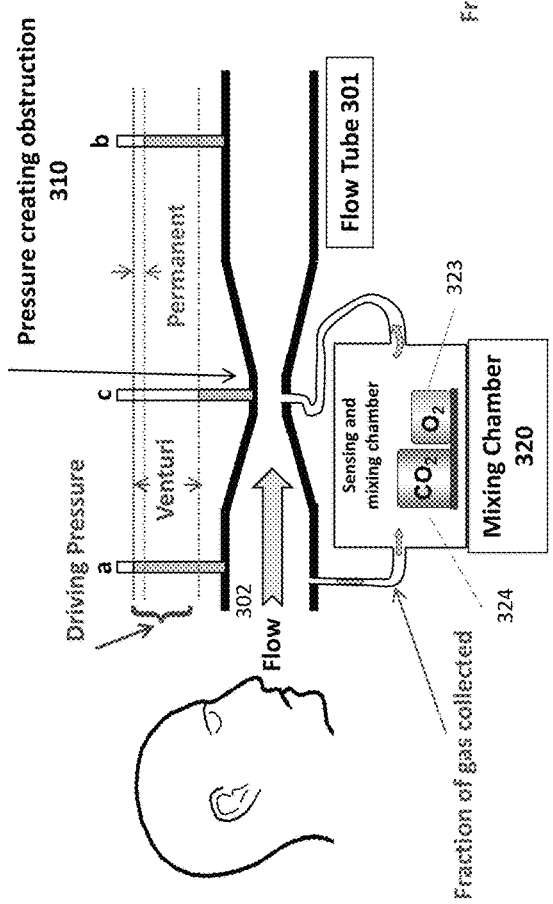

FIGS. 3C and 3D illustrate how pressure differentials during exhalation (FIG. 3C) and inhalation (FIG. 3D) in a flow tube can be used to passively, proportionally sample a person's breath with a valveless mixing chamber in a closed-loop metabolic collection system. The system is illustrated as a straight flow tube with a delivery and return port placed at locations to deliver gas to the sample/mixing chamber during exhalation and to collect little to no gas during inhalation.

FIGS. 3E and 3F shows the flow tube of FIGS. 3A and 3B with the inhale and exhale ports reversed.

Figures 4A, 4B, 4C:
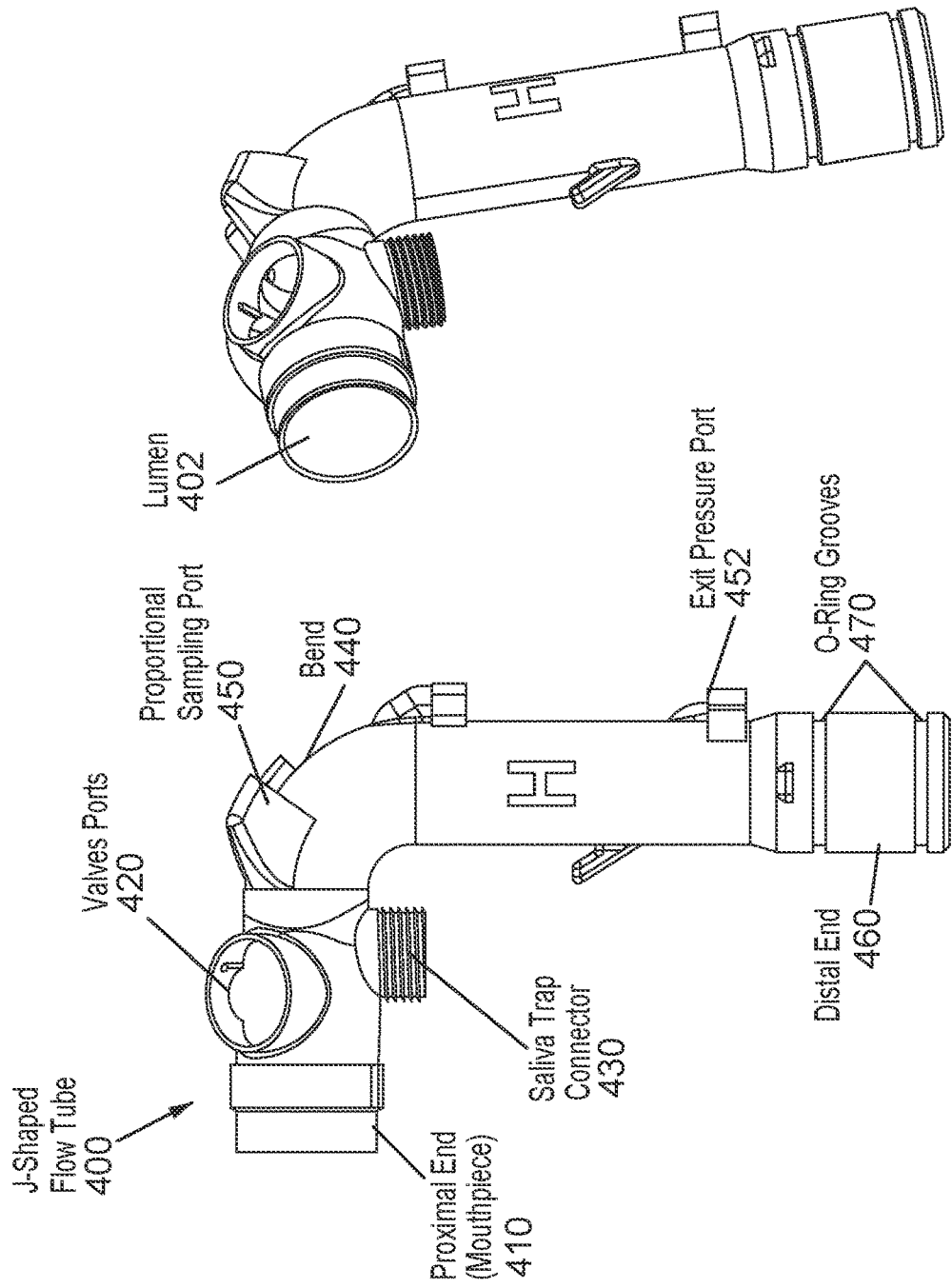

FIG. 4A is a view of first side of a high-flow, bent/curved flow tube for a closed-loop sampling system.

FIG. 4B is a perspective view of the bent flow tube of FIG. 4A.

Figure 1B:
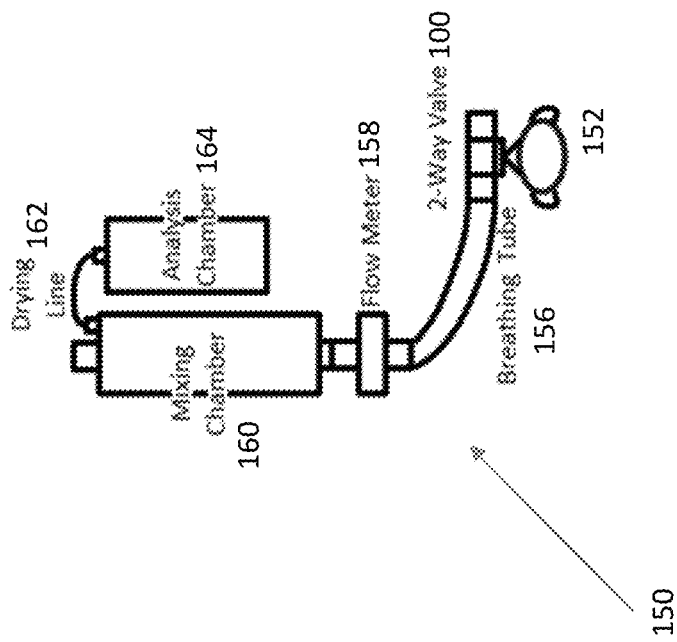
FIG. 1B shows a schematic of a metabolic cart.
Figure 1A:
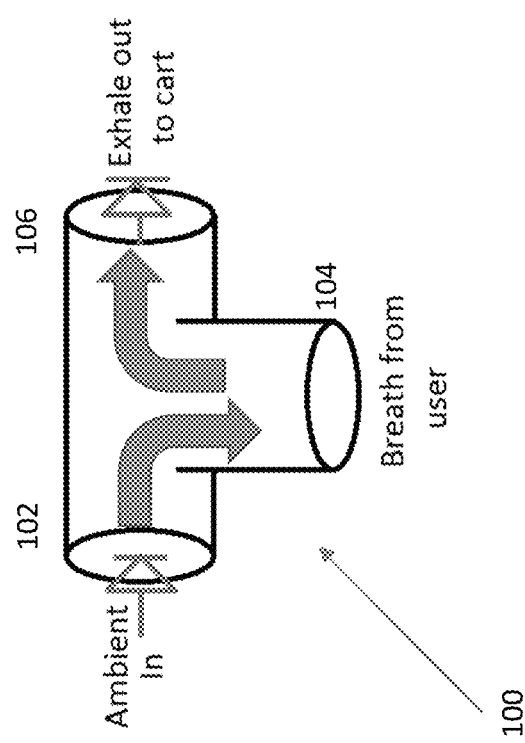
FIG. 1A shows a schematic of a unidirectional mouthpiece.

FIG. 4C is a view of a second side of the bent flow tube of FIG. 1A.

Figure 4F:
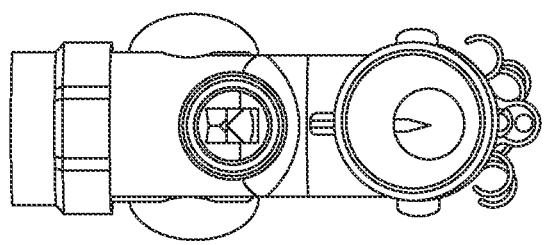
Figure 4E:
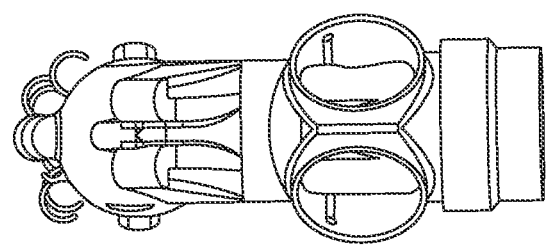
Figure 4D:
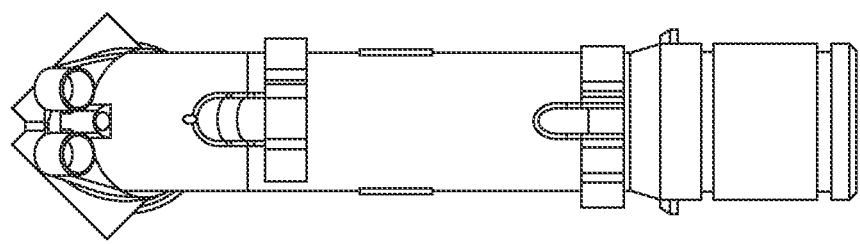

FIG. 4D is a view of a third side of the bent flow tube of FIG. 1A.

FIG. 4E is a top view of the bent flow tube of FIG. 1A.

FIG. 4F is a bottom view of the bent flow tube of FIG. 1A.

Figure 4H:
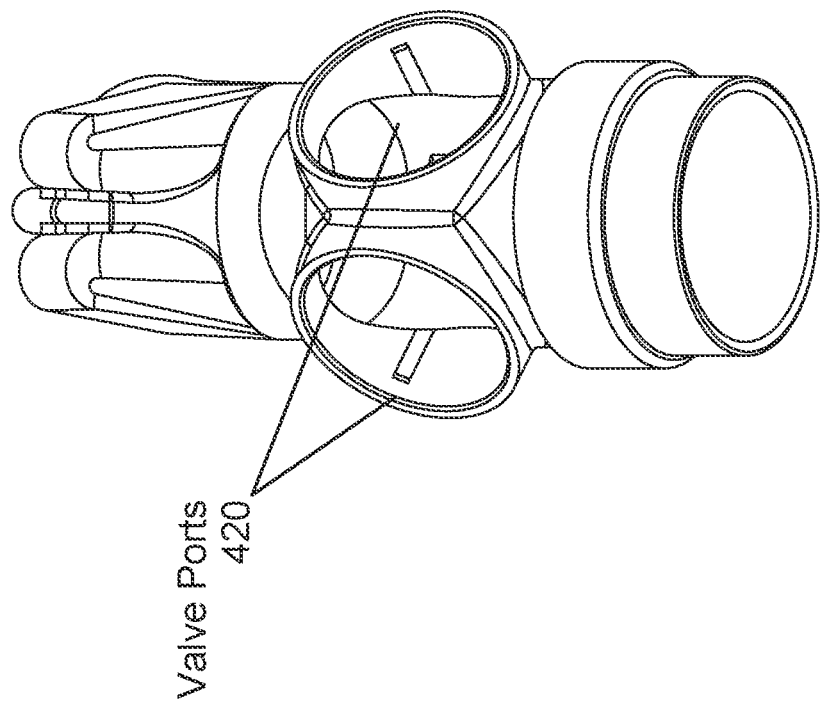
Figure 4G:
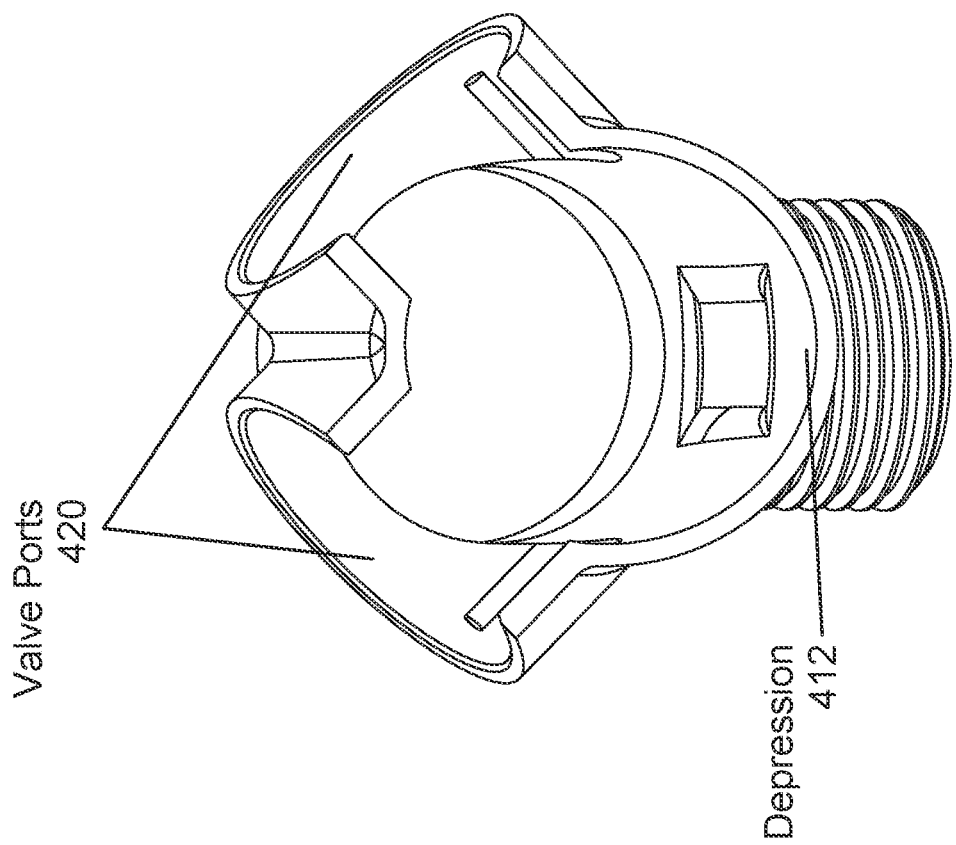

FIG. 4G is a cutaway view of the mouthpiece of the bent flow tube of FIG. 1A.

FIG. 4H is another perspective view of the bent flow tube of FIG. 1A.

Figure 4I:
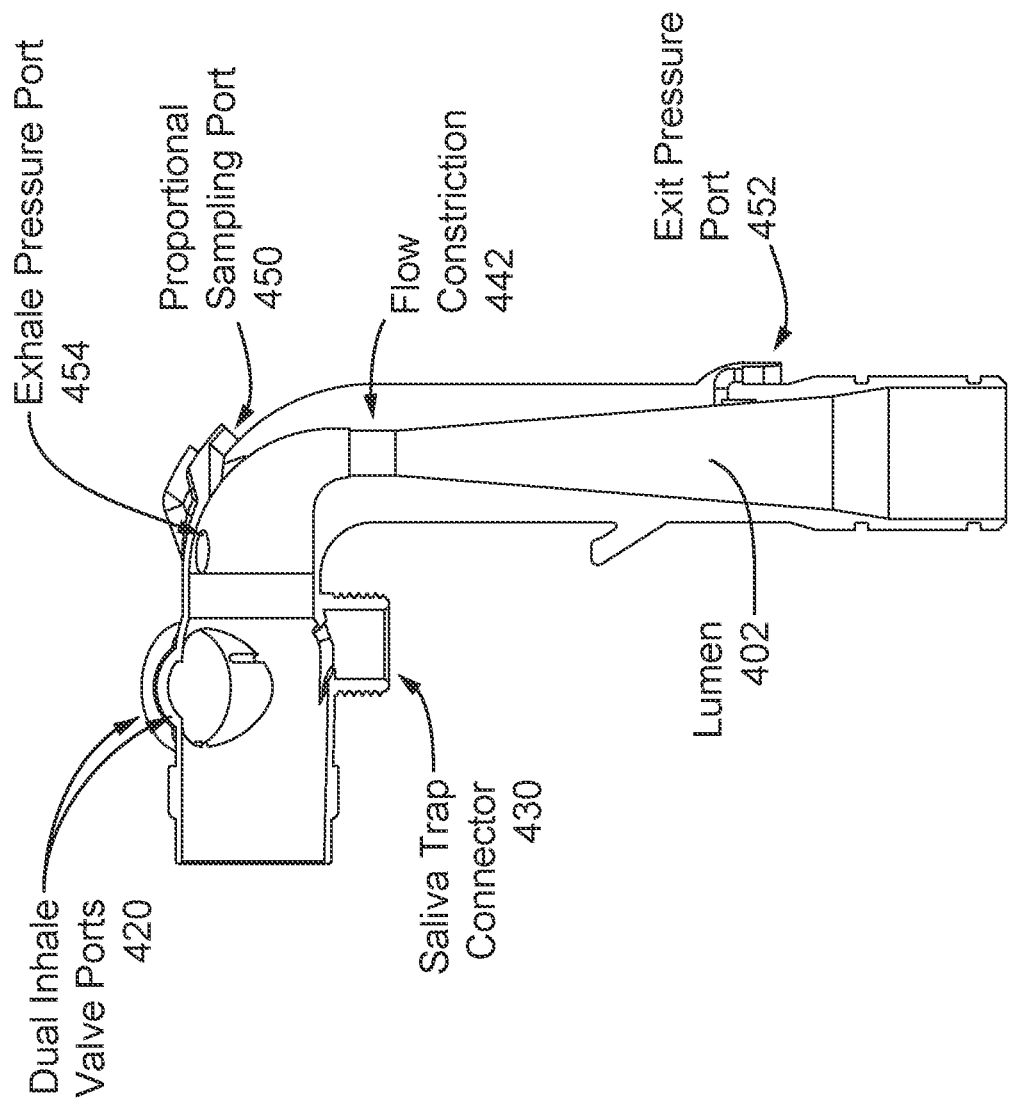

FIG. 4I a cutaway profile view of a bent flow tube similar to the one shown in FIG. 4A. It lacks a return port and is therefore suitable for use with a valved mixing chamber.

FIG. 4J is a perspective view of a bent, low-flow flow tube for a closed-loop sampling system.

FIGS. 4K and 4L show side views of a bent flow tube attached to a saliva trap and tubing that connects to a mixing chamber. Exhaled air passes unidirectionally out of the device, and some amount of flow occurs during inhale due to the cracking pressure of the valves.

Figure 4N:
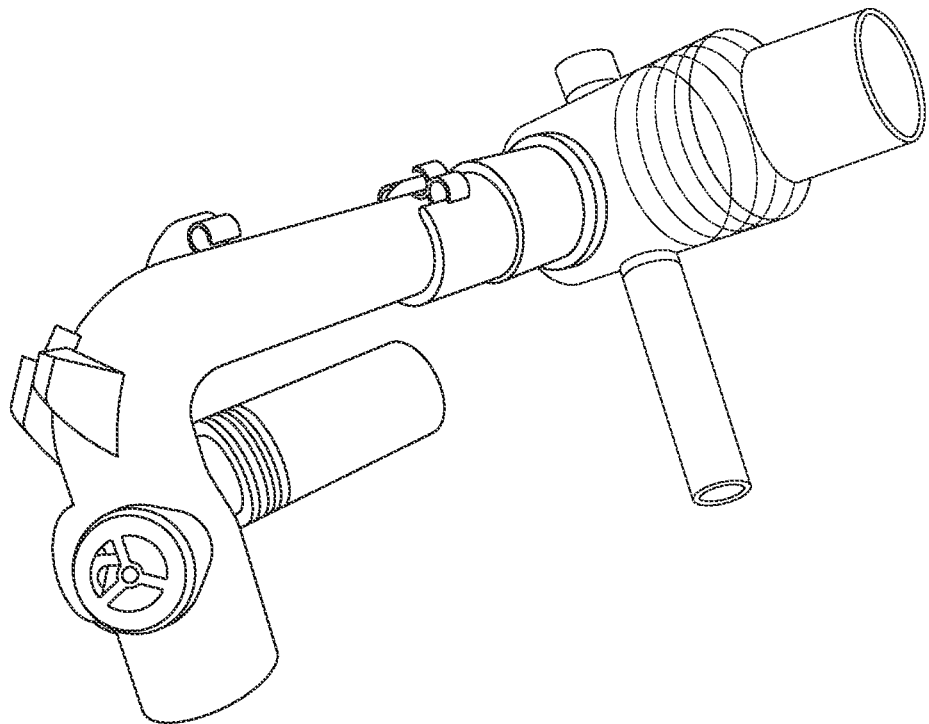
Figure 4M:
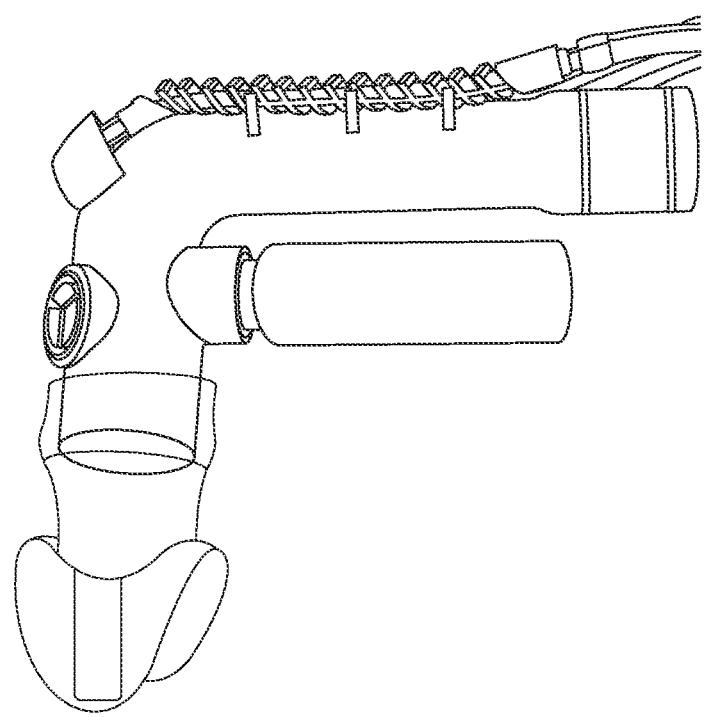

FIG. 4M is a photograph of a bent flow tube with a scuba-style mouthpiece, valves, and a saliva trap.

FIG. 4N is a photograph of a bent flow tube inserted into a Hans Rudolph valve.

Figure 5A:
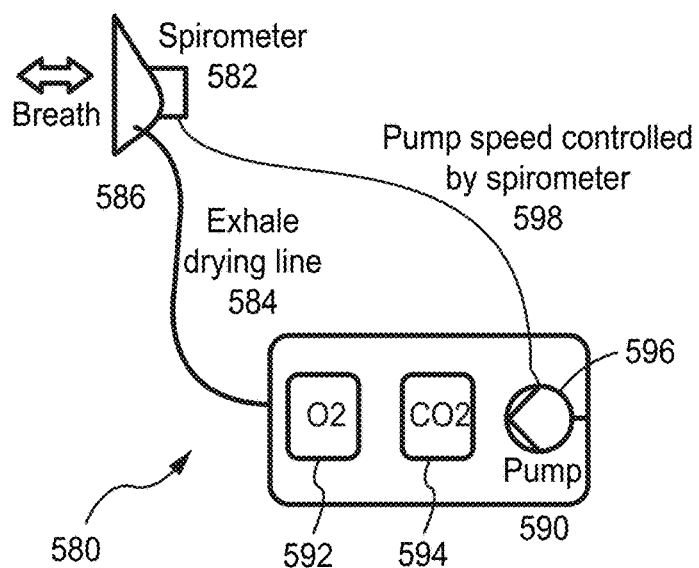

FIG. 5A is a schematic diagram of an active, breath-by-breath proportional sampling system.

Figure 5B:
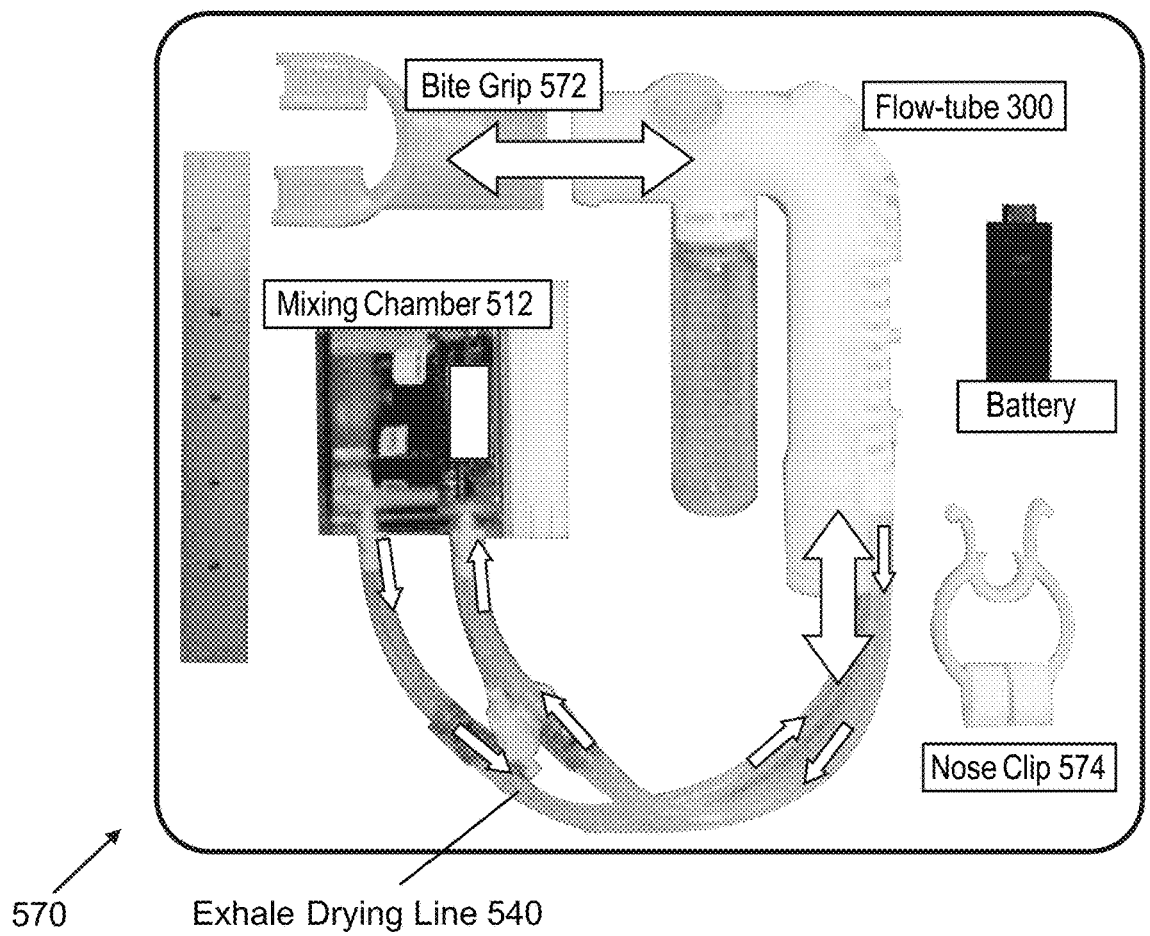

FIG. 5B is a photograph of a passive proportional sampling system that performs like the one in FIG. 5A, but without an active valve on the mixing chamber. This system behaves like the one shown in FIG. 5A but does not need an actively controlled pump.

Figure 5C:
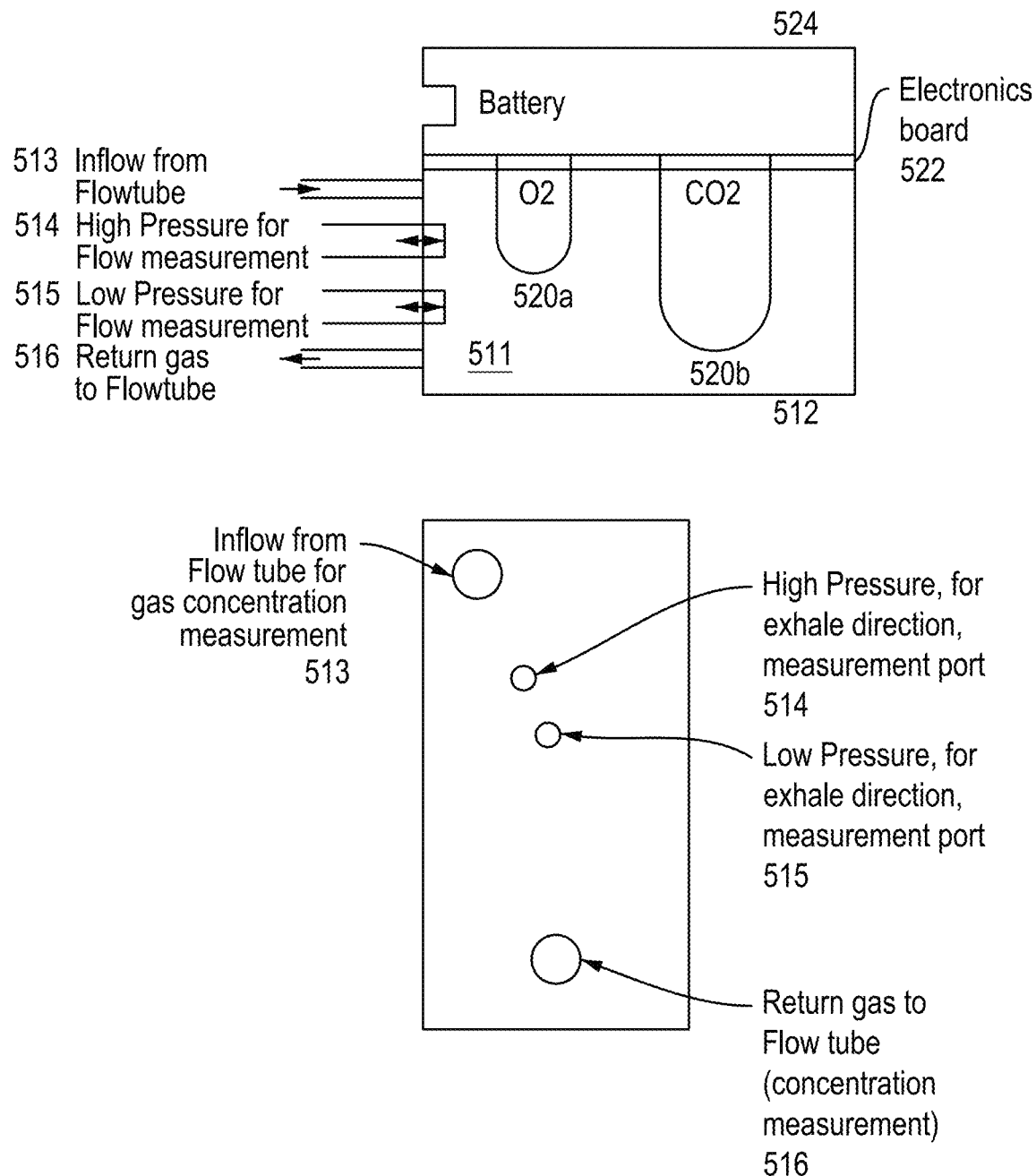

FIG. 5C shows a mixing (measurement) chamber suitable for use in the proportional sampling systems of FIG. 5B.

Figure 5D:
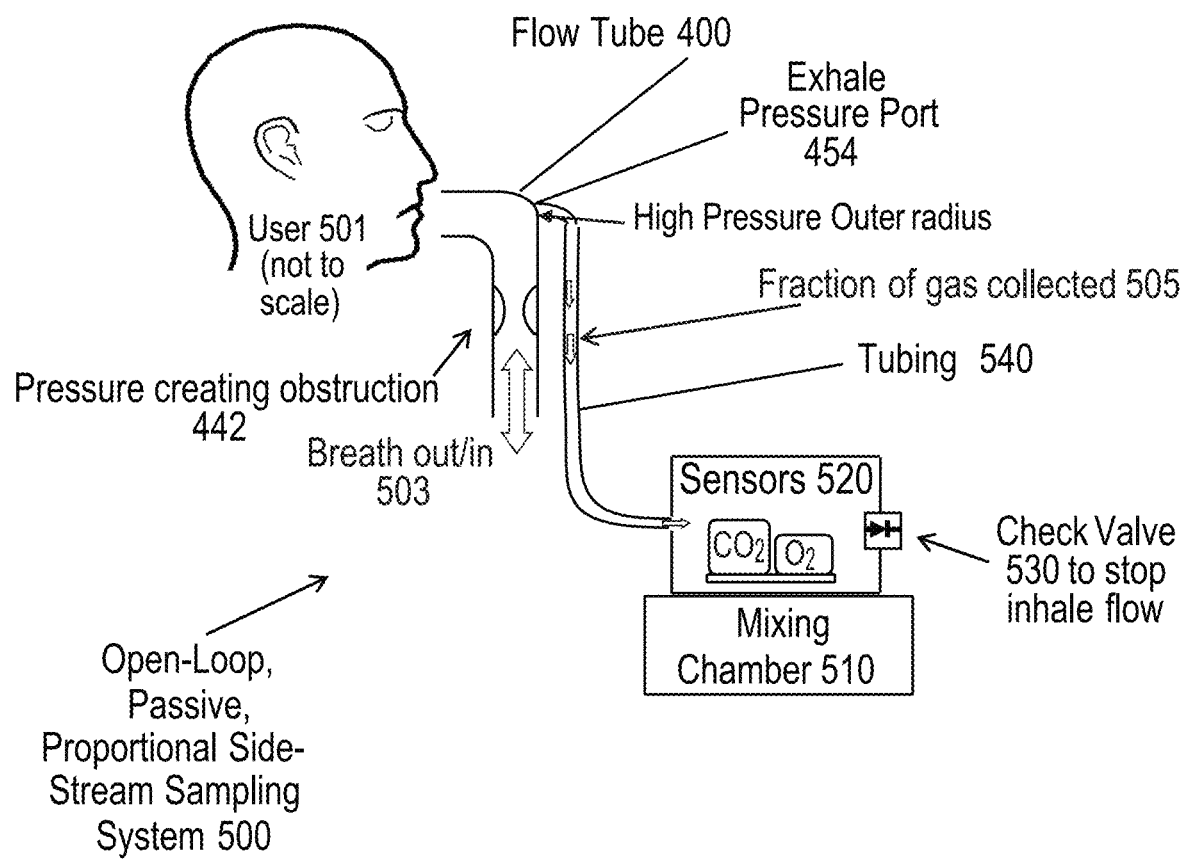

FIG. 5D is a schematic diagram of an open-loop sampling system with a bent flow tube and a valved mixing chamber. A pressure-creating obstruction 503 paired with a check valve 530 acts as the pump shown in FIG. 5A.

Figure 5E:
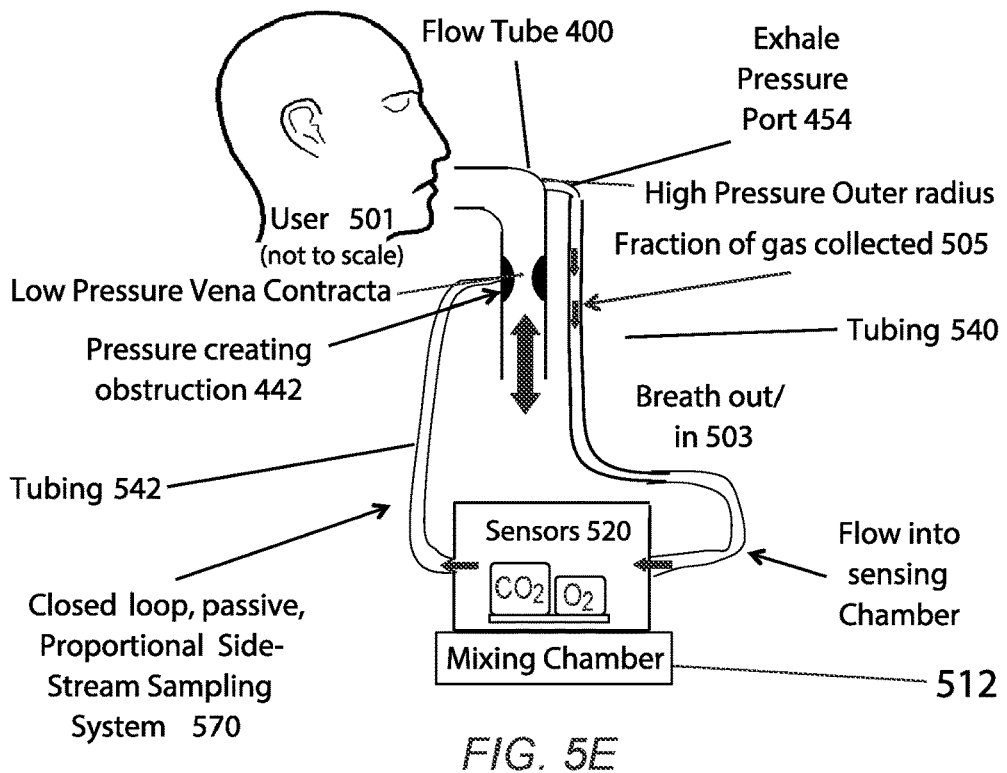

FIG. 5E is a schematic diagram of a closed-loop sampling system with a bent flow tube and a valveless mixing chamber.

Figure 5F:
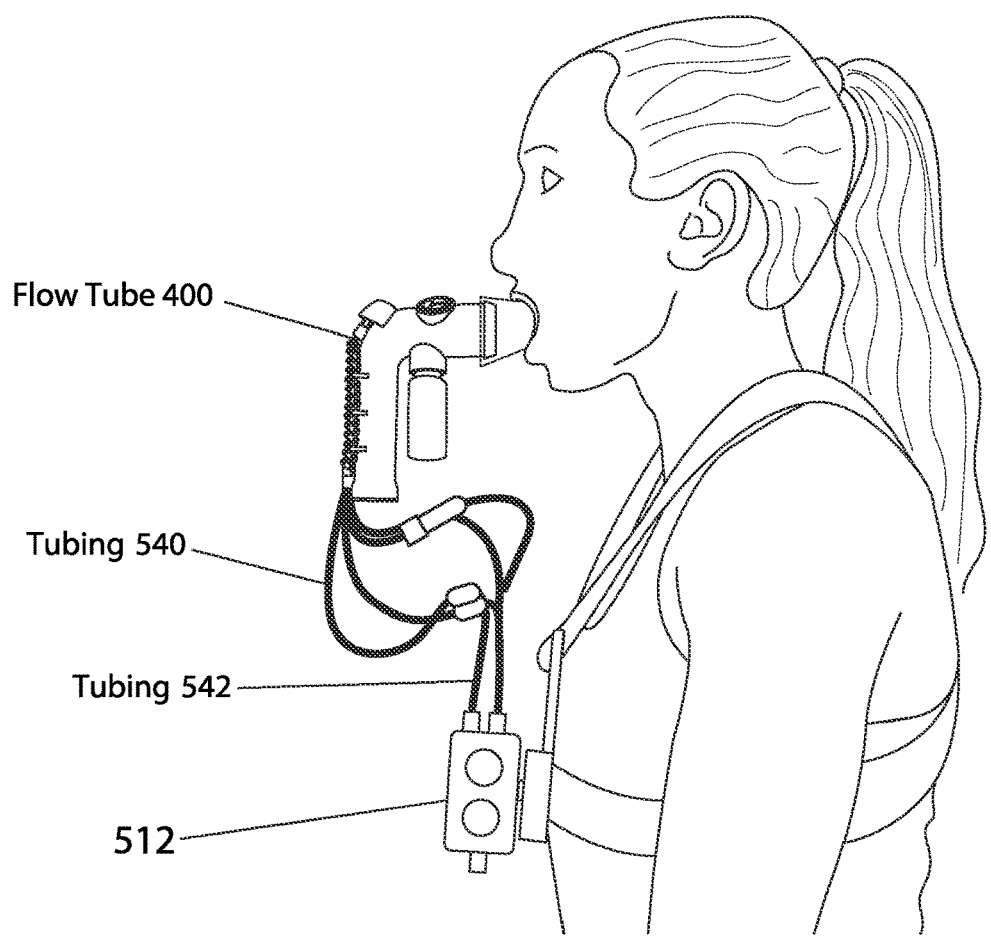

FIG. 5F is a photograph of a woman wearing a closed-loop sampling system with a bent flow tube attached to a valveless mixing chamber as in FIG. 5E.

Figure 6:
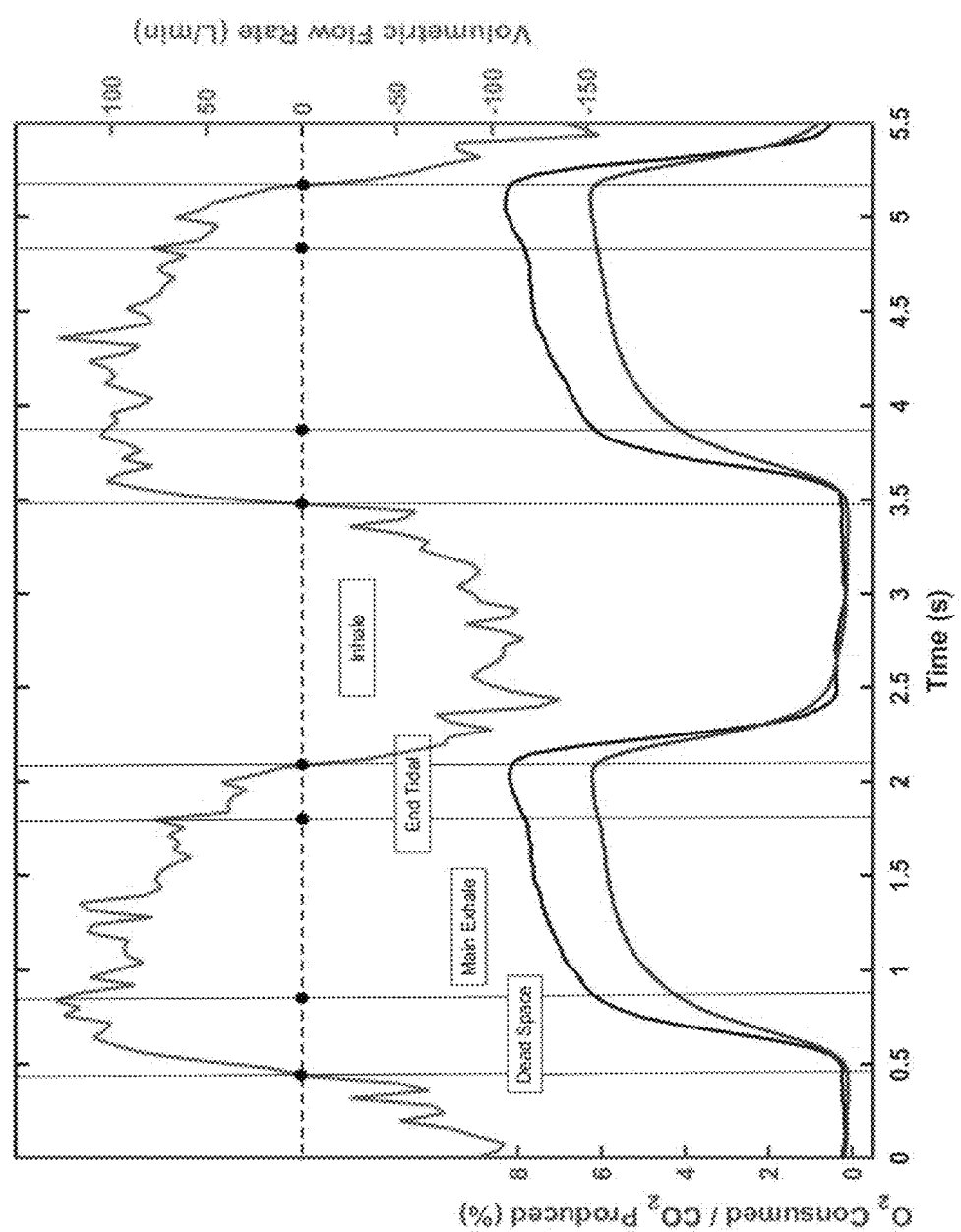

FIG. 6 shows two breath exhale cycles and identifies the epochs comprising a typical breath cycle as well as the parameters of interest.

Figures 7A, 7B:
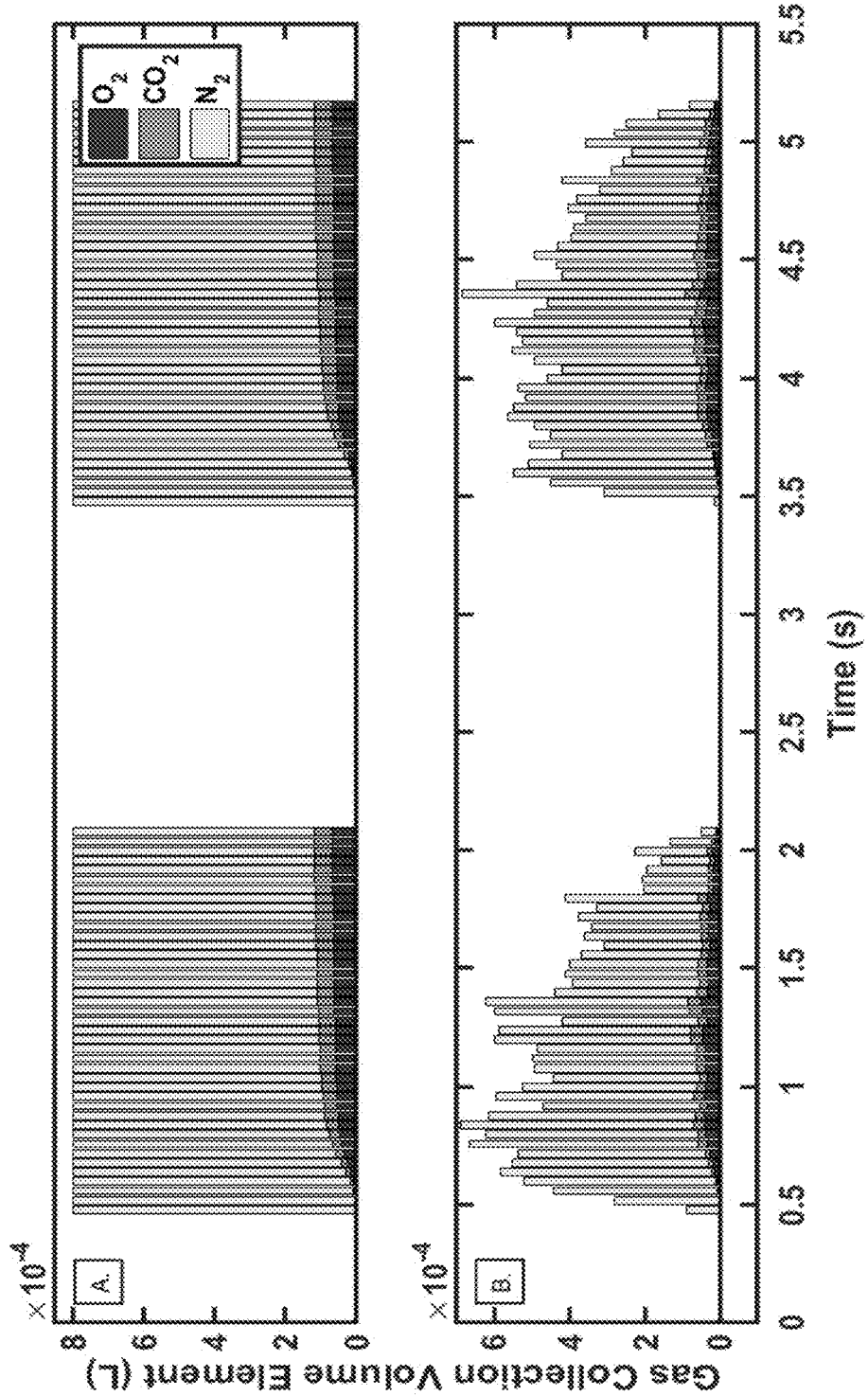

FIGS. 7A and 7B are bar charts showing the gas collection differential volume elements (DVEs) for constant rate versus proportional pumping methods.

Figure 8:
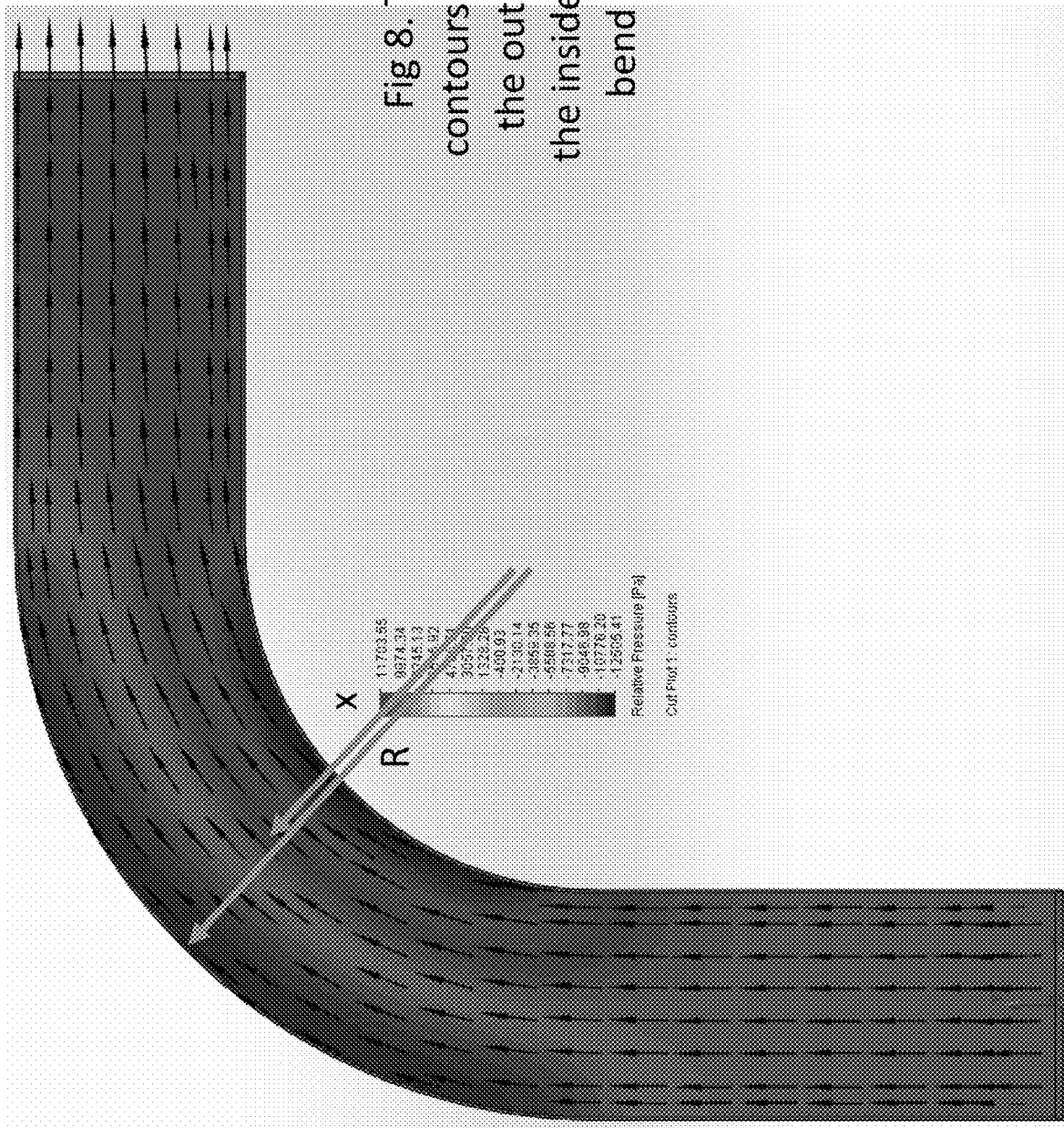

FIG. 8 shows the velocity fields and pressure generated for a nearly dissipation-free flow around a 90-degree bend, e.g., as in the flow tube of FIGS. 3A and 3B.

Figure 9:
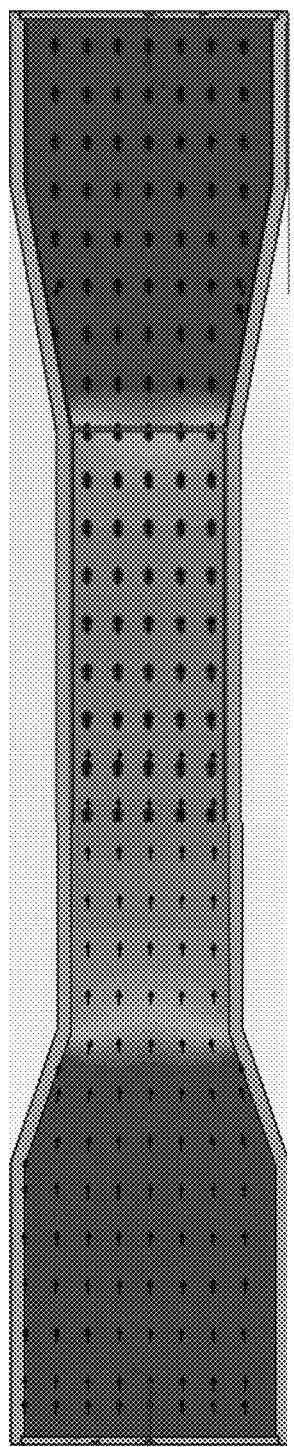

FIG. 9 shows the velocity fields and pressure generated for a nearly dissipation-free flow through a restriction.

Figure 10B:
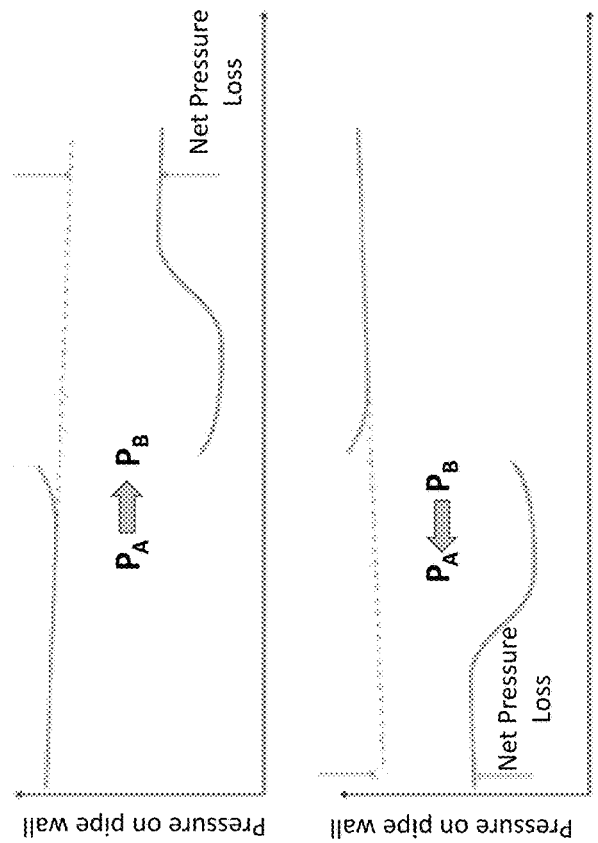
Figure 10A:
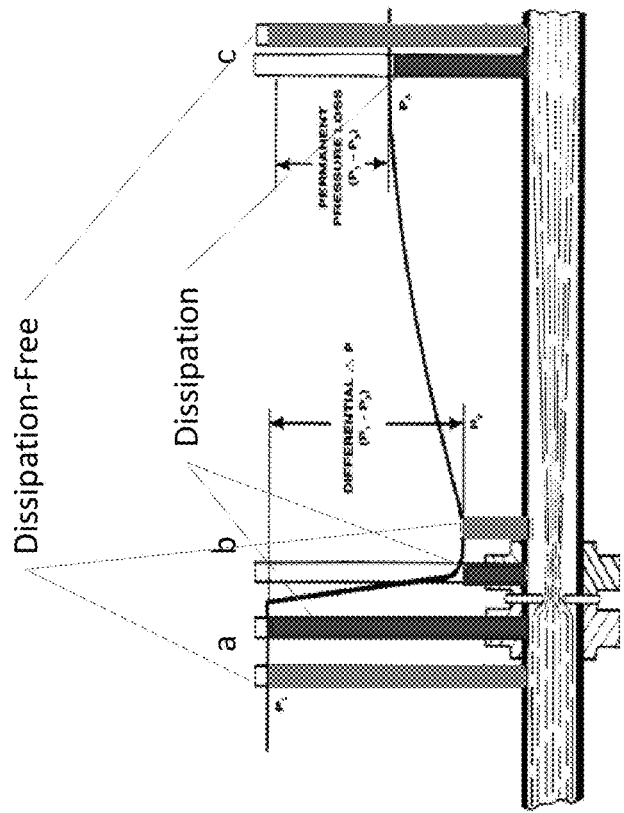

FIG. 10A shows a diagram of an orifice plate placed in a horizontal fluid flow from left to right through a conduit or lumen.

FIG. 10B is a more detailed plot of the pressure change through an orifice plate.

Figure 11:
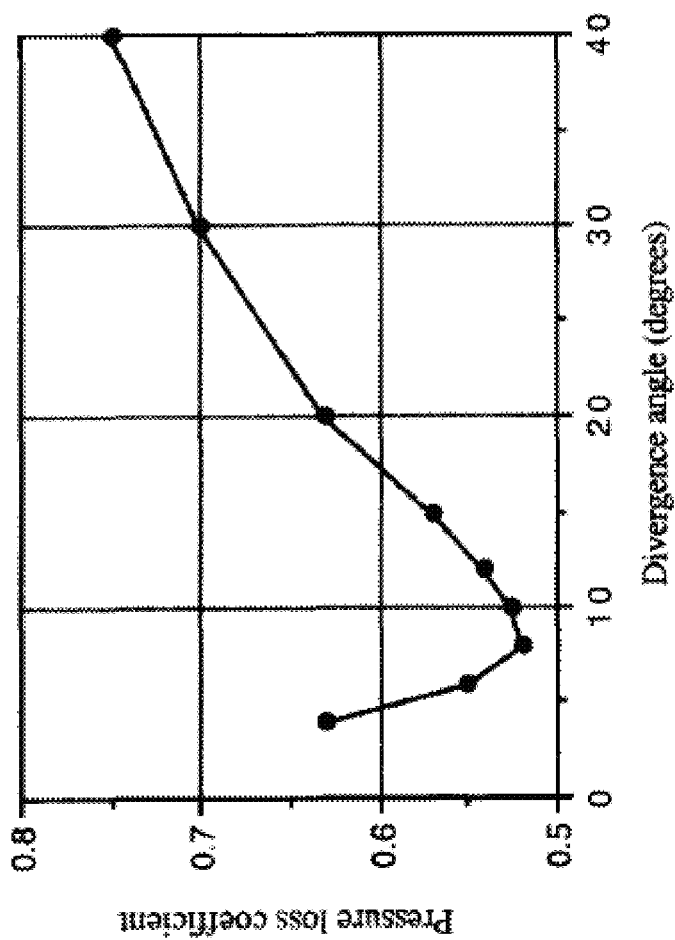

FIG. 11 is a plot of pressure lost for a cone-shaped diffuser as a function of the diffuser cone divergence angle. There is a minimum in pressure loss at a cone divergence angle of around 9 or 10 degrees, and the pressure loss is greater on either side of the inflection point.

FIG. 12 shows the different levels of stall in flow through a diffuser. These flow patterns are responsible for variations in pressure recovery.

Figure 13:
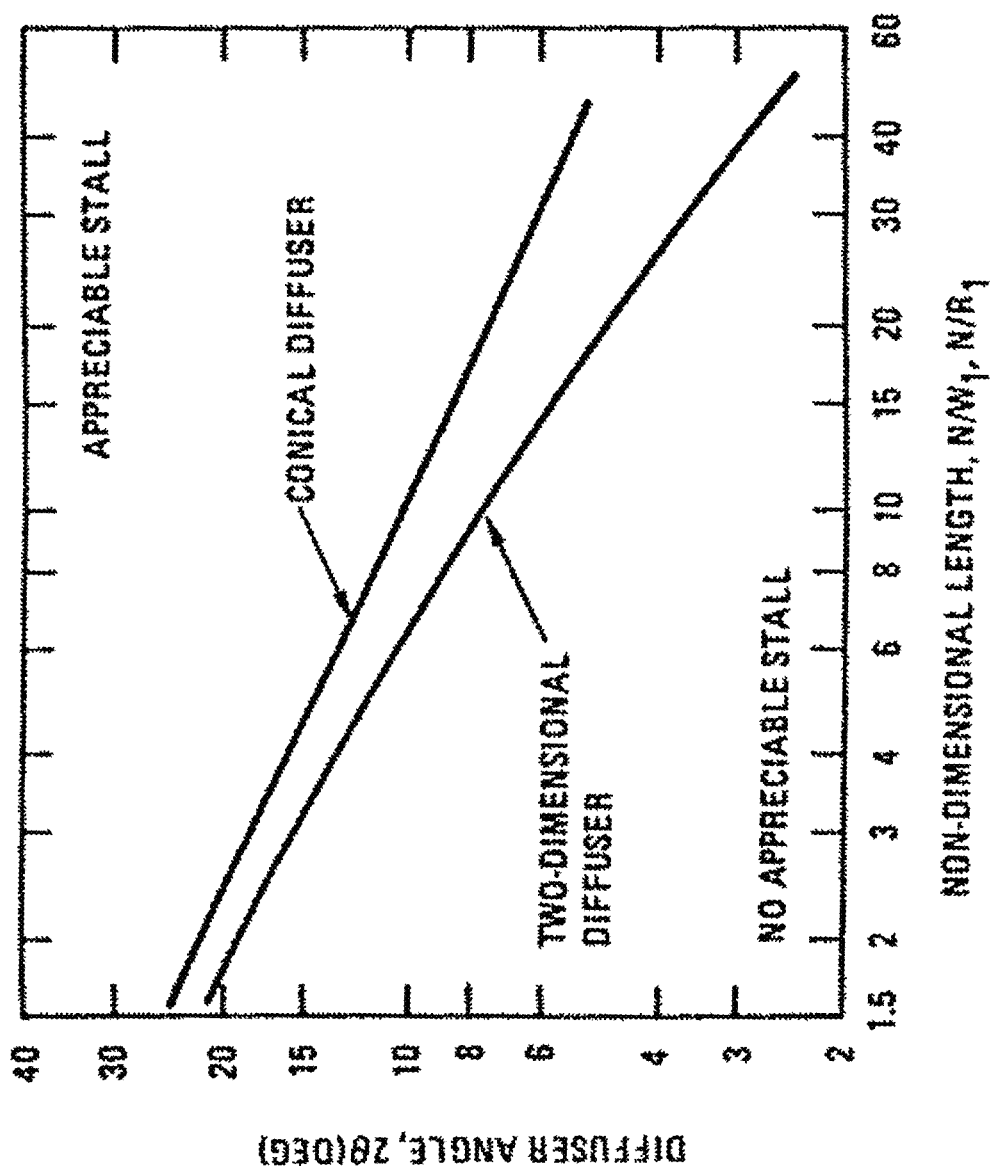

FIG. 13 is a plot of diffuser angle versus normalized length for conical diffusers (e.g., as in the flow tube of FIGS. 3A and 3B) and two-dimensional diffusers.

Figure 14:
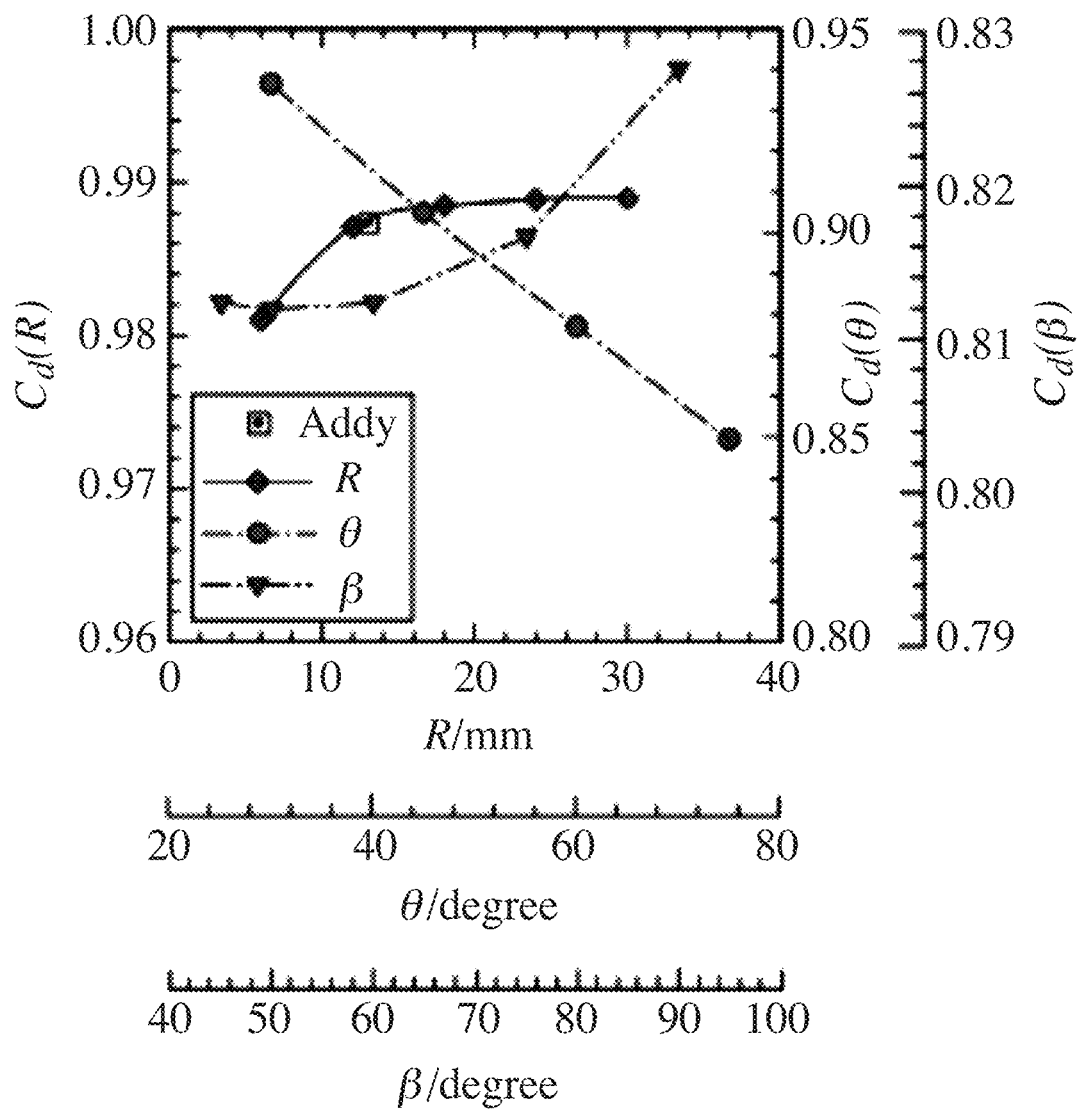

FIG. 14 is a plot showing the stability of the discharge coefficient for nozzles of differing geometries.

Figure 15:
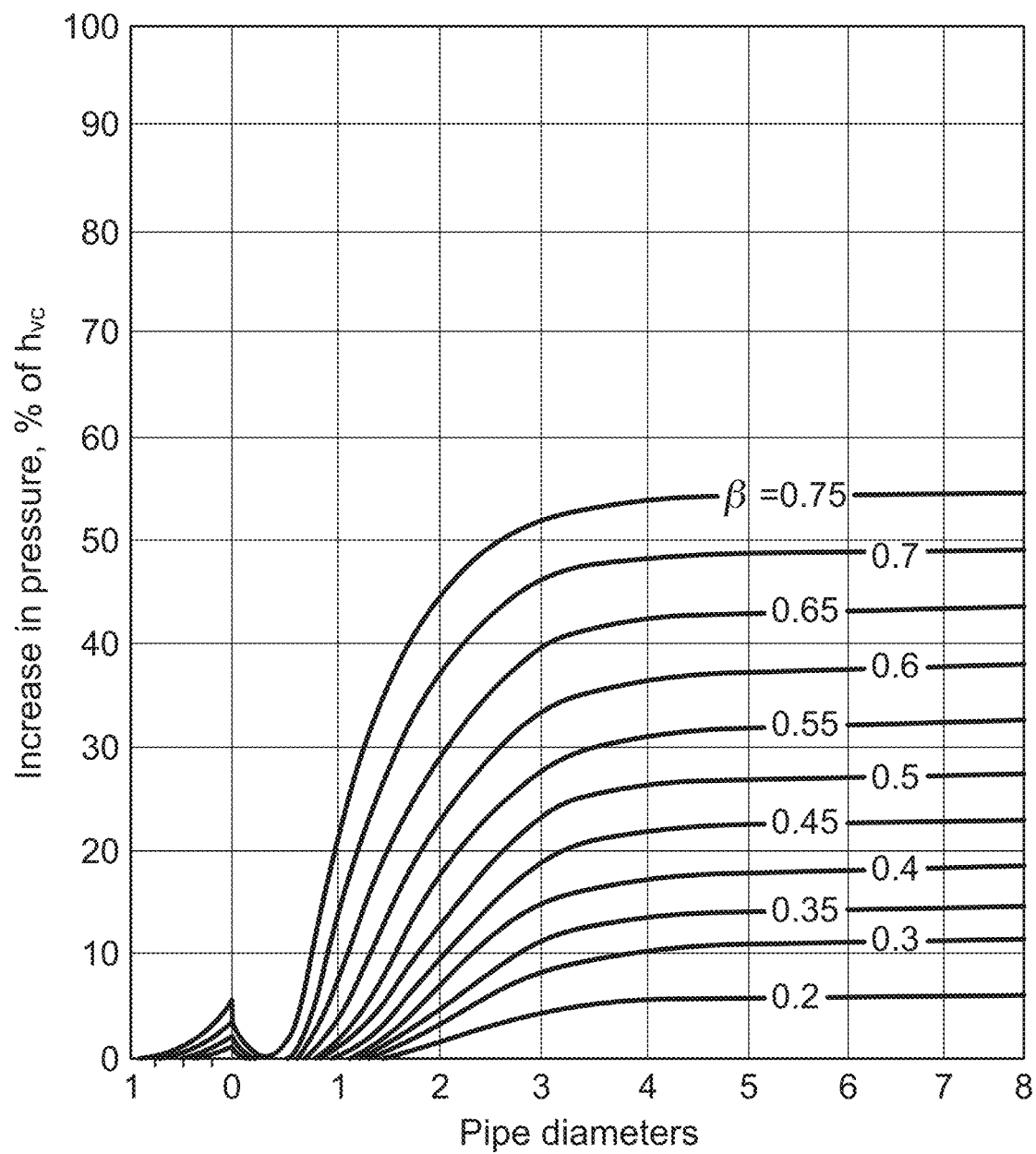

FIG. 15 is a plot showing the pressure recovery from the minimum pressure point in for flow through an orifice.

Figure 16B:
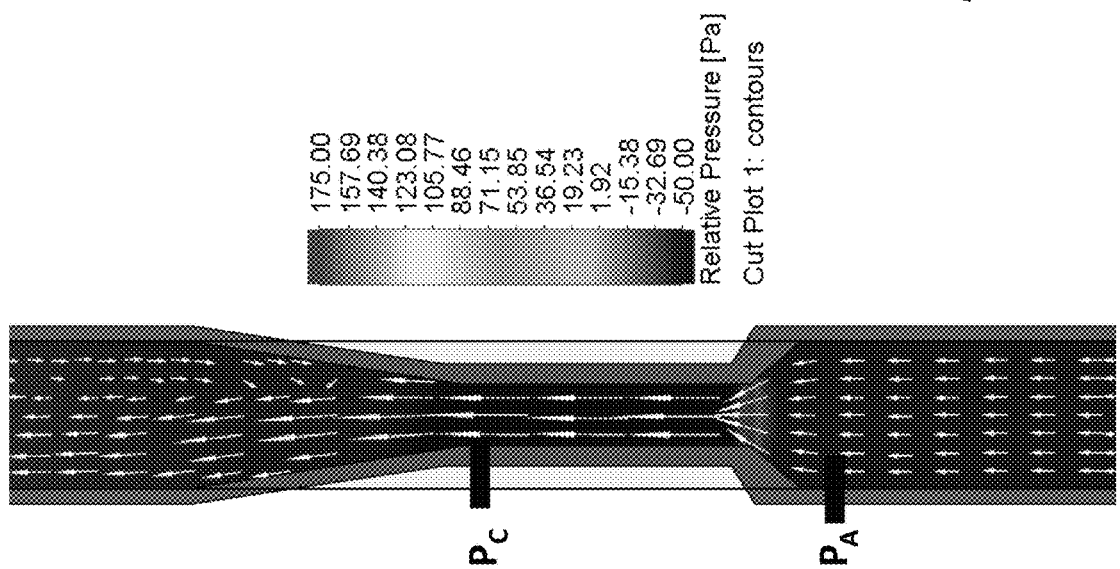
Figure 16A:
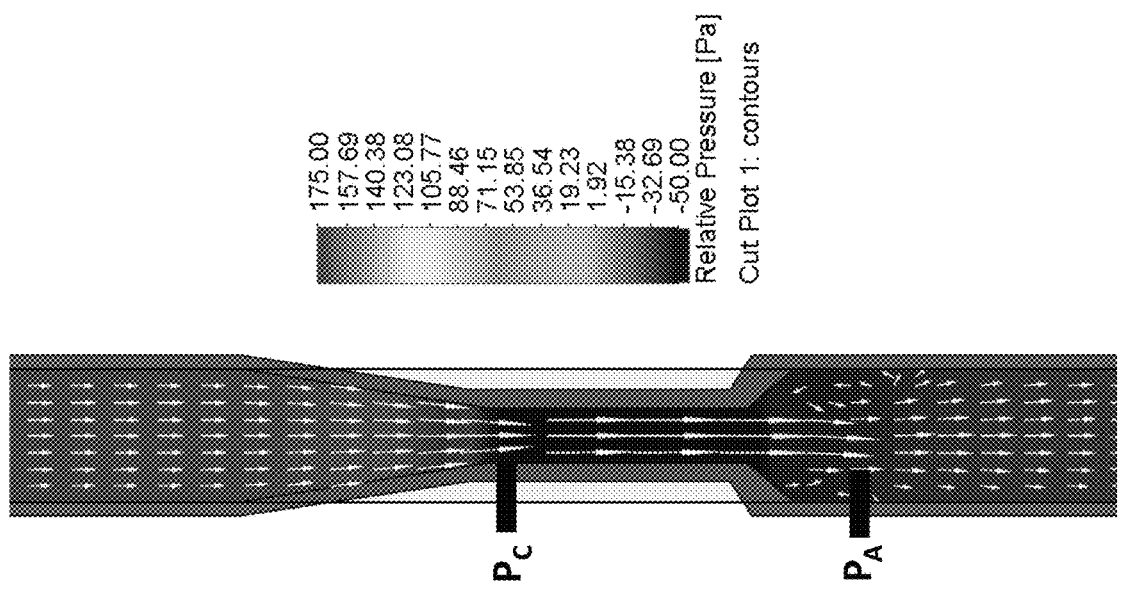

FIGS. 16A and 16B shows SolidWorks simulations of the pressure and velocity fields inside of an asymmetric constriction geometry for flow in opposite directions (down in FIG. 16A and up in FIG. 16B).

Figure 17:
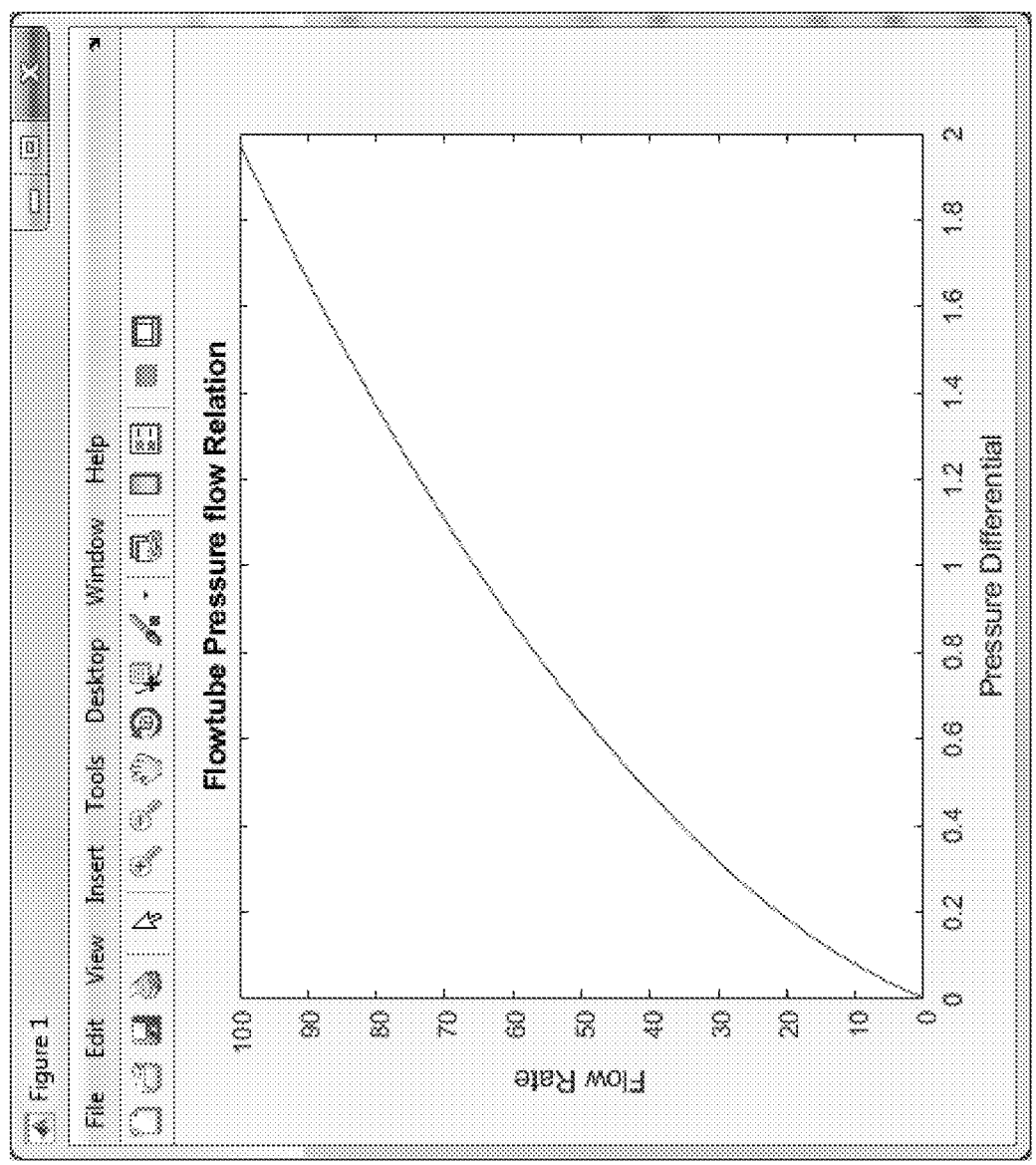

FIG. 17 is a plot of the measured gas flow rate as a function of pressure differential across the flow tube for a generic sensor.

Figure 18C:
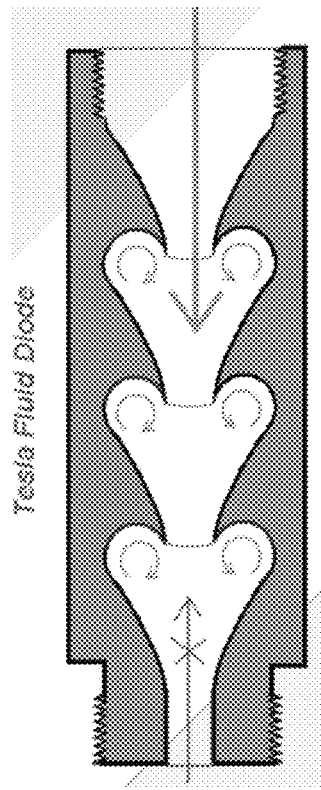
Figure 18A:
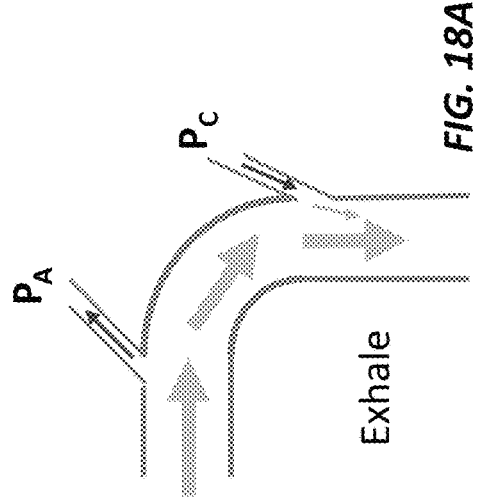
Figure 18B:
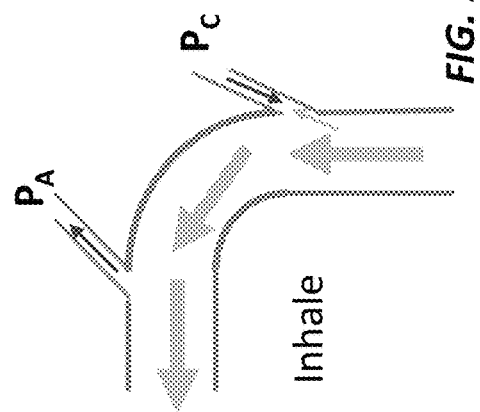

FIGS. 18A and 18B shows a secondary method of reducing the amount of flow into the auxiliary chamber when the flow tube is used as a collection device.

FIG. 18C shows a design for a Tesla flow diode which uses the principle illustrated in FIGS. 18A and 18B to create mono-directional flow.

Figure 19:
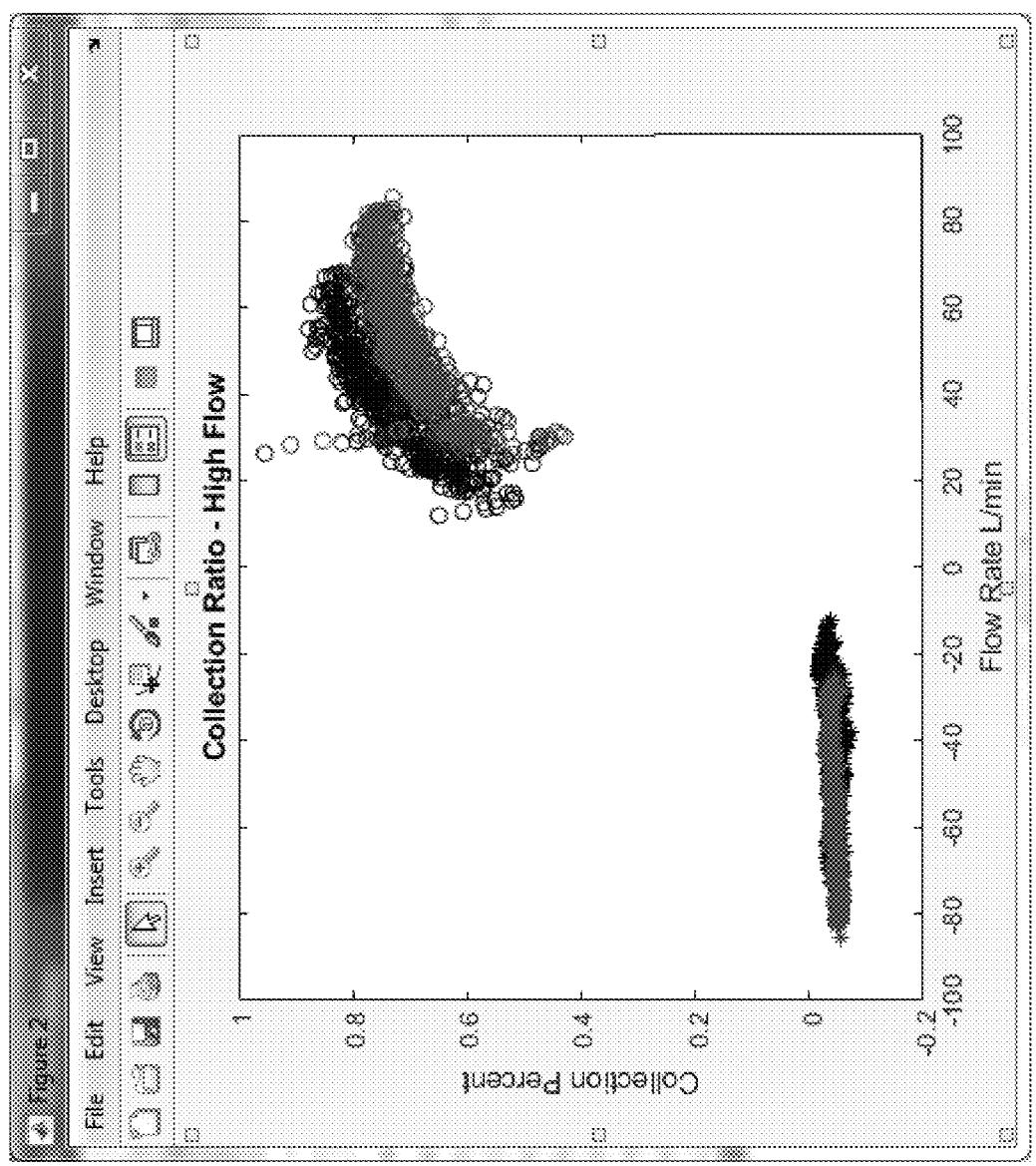

FIG. 19 is a plot showing the effectiveness of the passive proportional valveless sampling technique for three different high-flow flow tubes like the one in FIGS. 3A and 3B.

Figure 20:
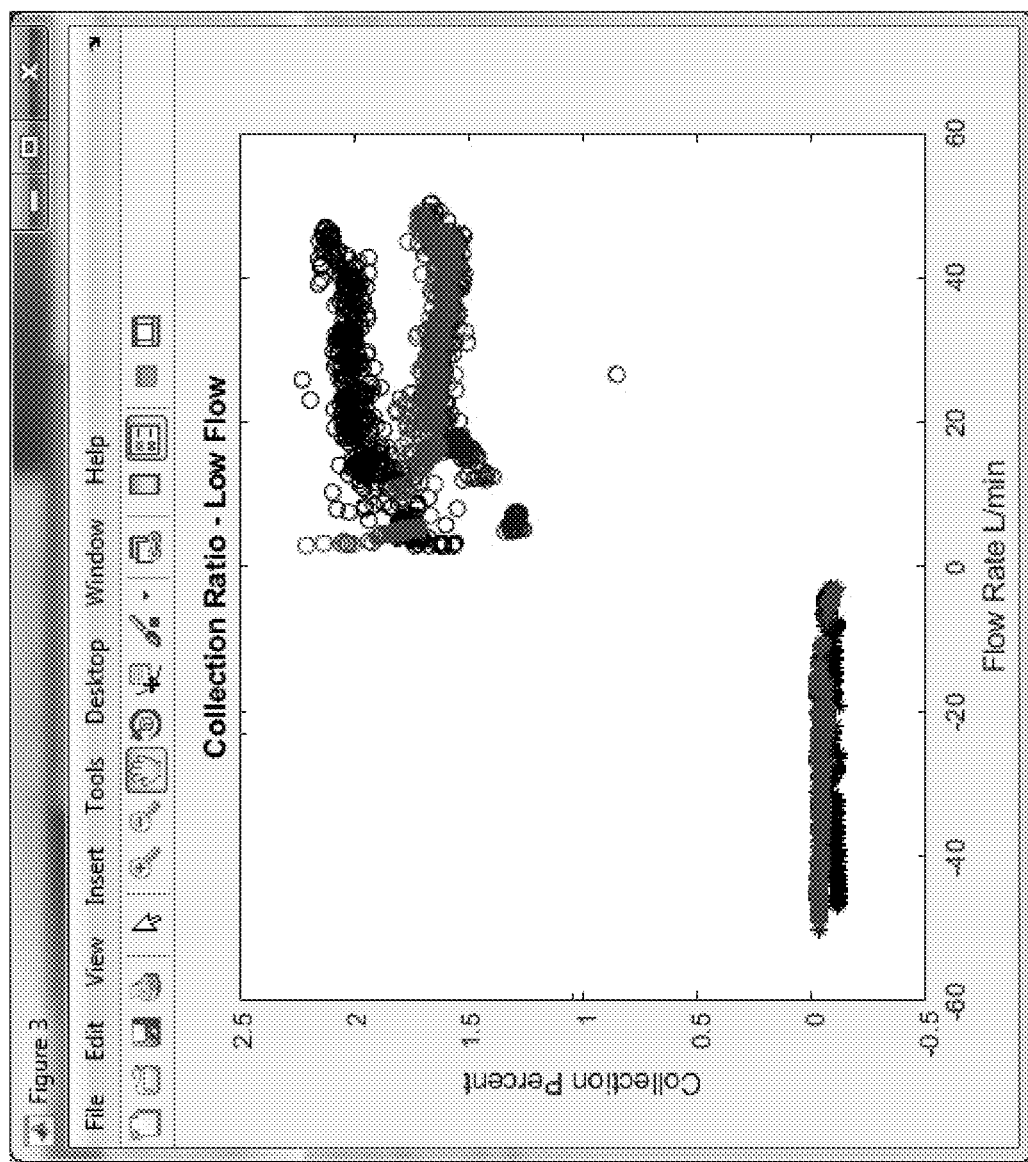

FIG. 20 shows the same data set as FIG. 19, but for a flow tube like the one in FIGS. 3A and 3B with a higher respiratory burden.

Figure 21:
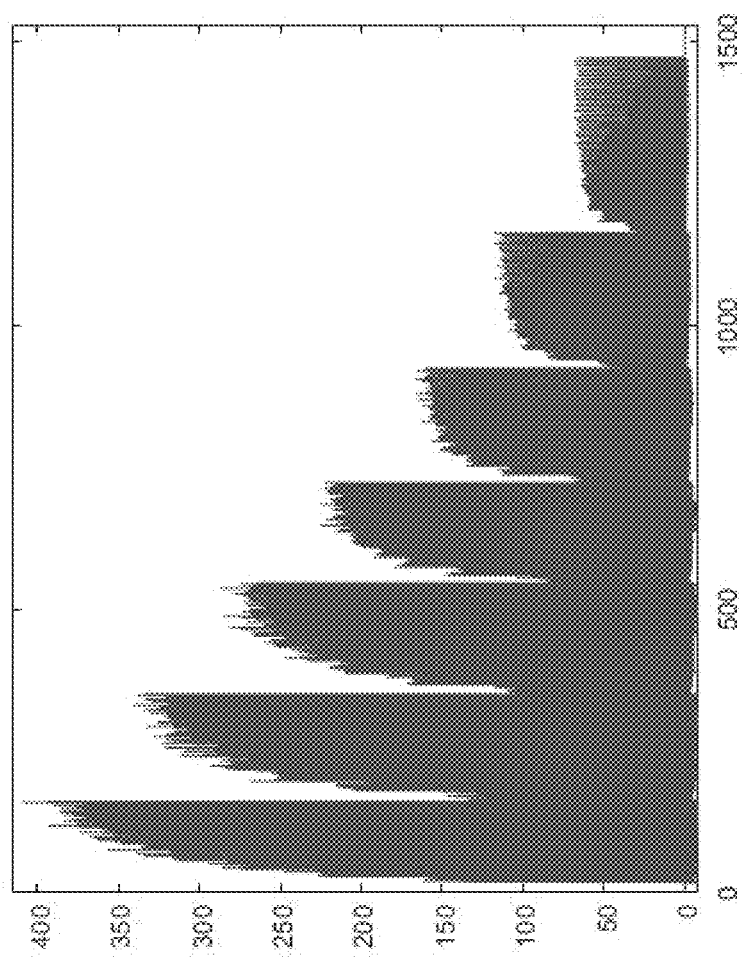

FIG. 21 shows the raw data used to estimate or determine the volume of exhale/inhale entering the collection chamber in the passive side stream sampling system of FIG. 5B. It shows that the flow rate of gas entering the chamber varies over many breathing cycles, starting from rapid flow at the beginning to slower flow by the end.

Figure 22:
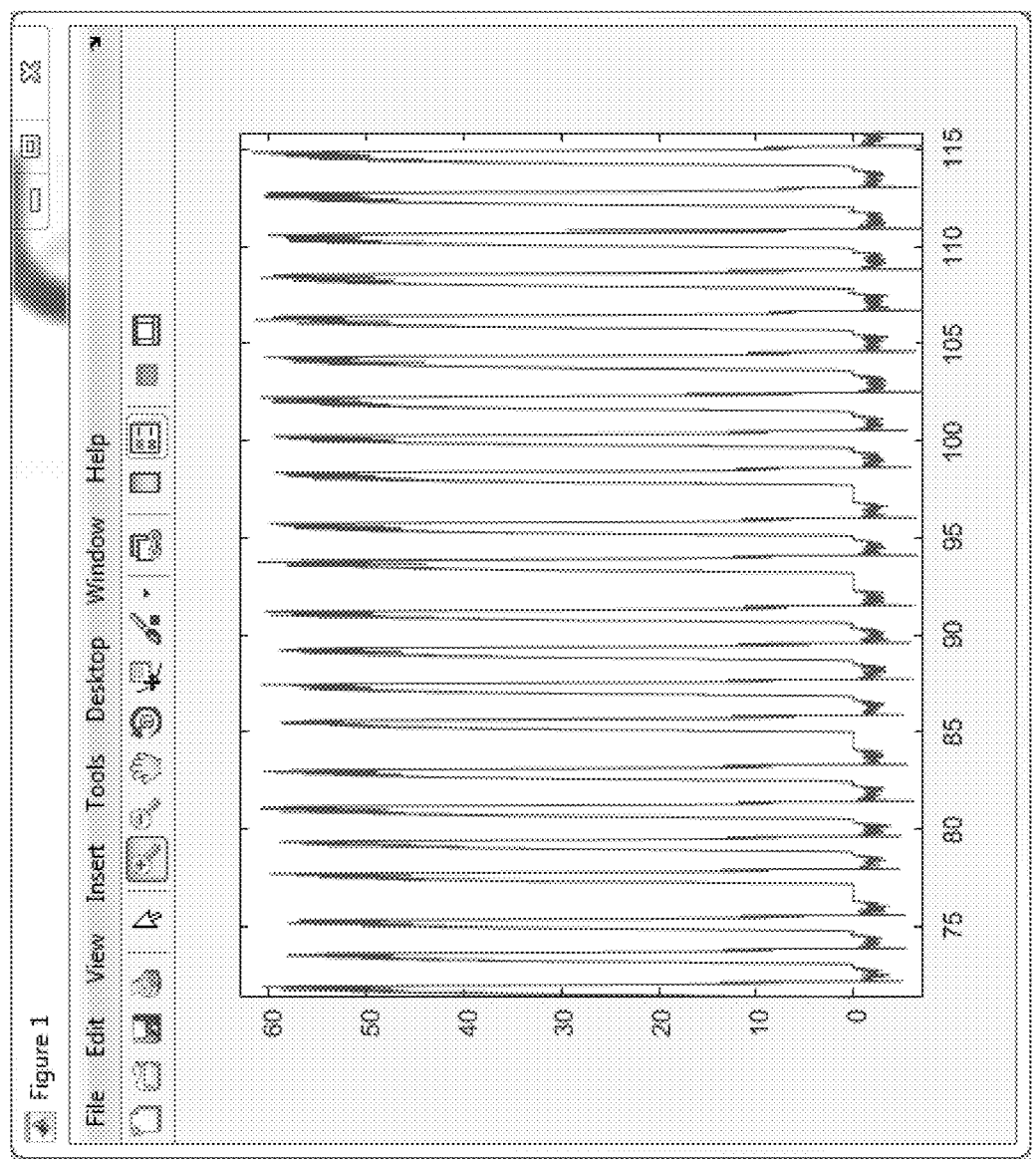

FIG. 22 is a close-up of a few breathing cycles from FIG. 21.

Figure 23A:
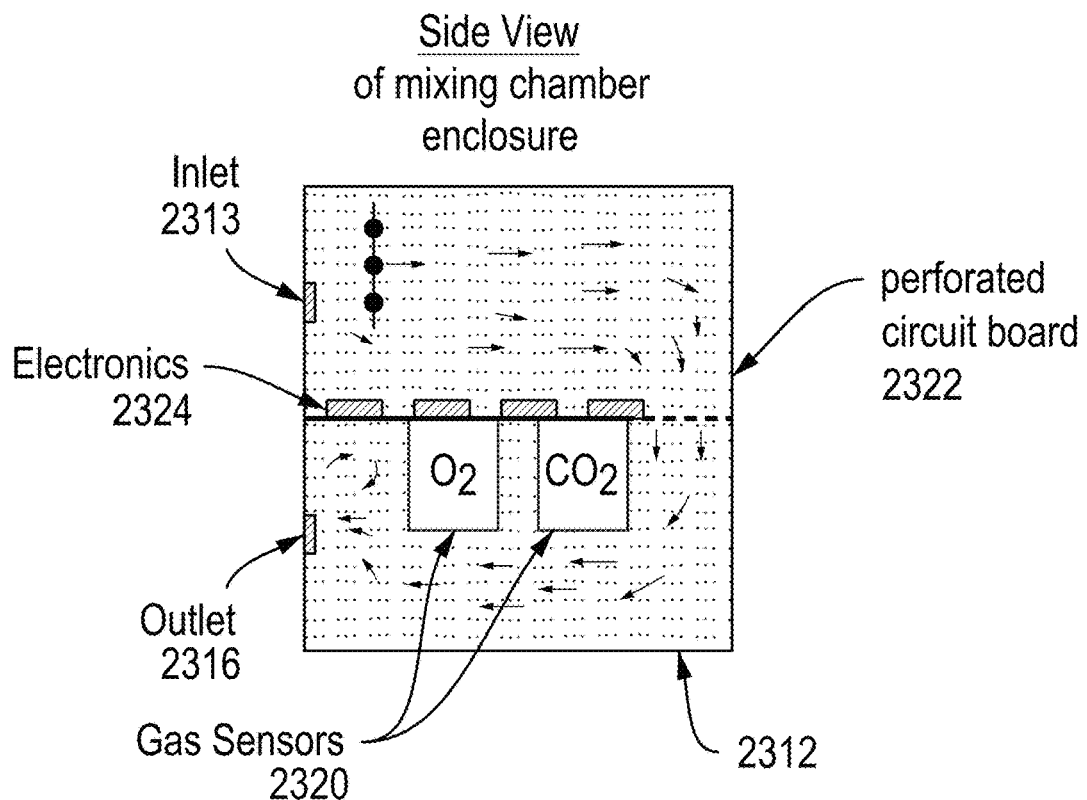

FIG. 23A is a cross-sectional view of the mixing chamber illustrating a perforated baffle and perforated circuit board disposed therein, which aid in mixing the expired boluses of gas before same arrive at the at sensor(s).

Figure 23B:
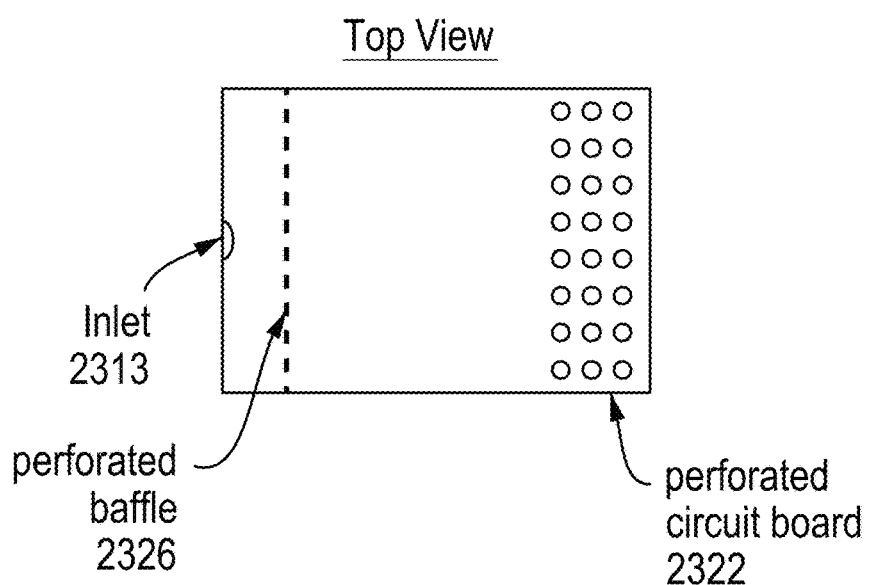

FIG. 23B is a top, cut-away view of the mixing chamber and perforated circuit board shown in FIG. 23A.

DETAILED DESCRIPTION

Inventive embodiments include a low-cost sensor that combines features from the breath-by-breath and metabolic carts. This sensor uses an innovative passive proportional side-stream gas collection mechanism to extract a small fraction from the exhale flow with an extraction rate that is directly proportional to the exhale flow rate. This proportionality remains stable or constant over the entire exhalation, regardless of the flow rate or pressure—for instance, the passive proportional side-stream gas collection mechanism may extract 1% of the exhaled breath over the entire pressure/flow rate range of the exhaled breath. This percentage or proportion may vary slightly with respiration rate or barometric pressure and falls to zero when the gas flows in the reverse direction (i.e., when the subject inhales).

By diverting a small proportional sample from the main flow stream, rather than collecting the entire breath, the mixing chamber used to contain the breath sample is drastically reduced in size, from several liters to a fraction of a liter. However, by capturing a proportional sample of the breath, the fidelity of exhale breath gas concentrations is preserved: when converted to standard temperature and pressure (STP) conditions, the volume concentrations of gases in each exhaled breath fraction in the mixing chamber is the same as the volume concentrations of gases in the corresponding entire exhaled breath. As a result, sensors in the mixing chamber or coupled to the output of the mixing chamber can measure the gas properties and, if they're in the mixing chamber, act as flow mixing obstacles.

The exact percentage of exhaled breath siphoned out of the exhale flow may be set based on the size of a mixing chamber used to capture and average the exhaled breath fractions. The percentage may range from about 0.5% to about 2.5%, depending on the application and the size of the mixing chamber. For example, with a 1% proportionality, a nominal 3-liter mixing chamber can be shrunk by a factor of 100 to 30 mL. (A tradeoff between percentage and mixing chamber size is that smaller proportional samples fill the chamber more slowly.) For resting metabolic measurements, the percentage may be larger (e.g., more than 2%) to improve measurement fidelity; for making metabolic measurements during exercise, the percentage may be smaller (e.g., less than 1%) to reduce the respiratory burden. Smaller percentages may be possible for smaller mixing chambers or for more sensitive sensors, such as electro-chemical sensors.

The size of the mixing chamber varies with the percentage of extra breath siphoned out of the exhale flow, the number of breaths being averaged, and the speed of the sensors used to measure the gas concentrations. In general, the mixing chamber should be large enough to hold the volume equivalent of one full breath (also called the breath equivalent volume (BEV)) at a minimum and up to 5 to 10 BEVs. The mixing chamber can be larger, e.g., for capturing portions of a substantial number of breaths (say, 100 breaths or more) for longer averaging times (slower sensors), for eliminating confounds due to short perturbations in breathing, or for resolving ventilation/perfusion (V/Q) mismatch following postural changes.

The desired uncertainty of gas concentration measurements also affects mixing chamber size. The uncertainty is a function of the number of breath equivalents within the mixing chamber—the more breaths in the mixing chamber, the more accurate and repeatable the gas concentration measurement. From the perspective of optimizing performance, the gas concentration uncertainty should be comparable to the sensor uncertainty (and both should be as low as practically achievable). Other effects such as adsorption/desorption from internal surfaces are also important, but these should quickly stabilize during use.

The sensors can be fast (e.g., with response times of less than 500 milliseconds) or slow (e.g., with response times of more than 1 second). One benefit of the passive, proportional sampling is the ability to provide an extended dwell time with the proper gas mixture within the mixing chamber, allowing the use of slower, less expensive, more efficient, and often longer-lived gas sensors. In general, the gas sensor should be fast enough to sample the maximum rate-of-change in the gas concentration within (or just following) the mixing chamber at or above the Nyquist sampling rate, which is twice the maximum rate-of-change. The maximum rate-of-change is a function of the breathing rate, breathing (tidal) volume, proportional sampling fraction of the gas splitter, and mixing chamber volume. At a minimum, the sampling rating would be once per breath.

As an example, consider a breathing rate of 10 breaths per minute (bpm) (5 liters per minute (lpm) total), a tidal volume of 500 cc, a proportional sampling fraction of 1% for a sample flow of 50 cc/min into the mixing chamber, and a mixing chamber volume of 100 cc (a breath-equivalent volume (BEV) of 20). In this example, the gas exchange half-life is about 1 minute, because in 1 minute, the subject displaces half of the gas within that chamber (50% dilution). Assuming good mixing, in the second minute, the subject displaces 75% (100%+50%, with the sum divided by 2) of the gas within the mixing chamber. (Alternatively, think of this as a 20 BEV mixing chamber with a gas mixing time constant of 1 minute.)

The gas sensors can respond slowly, so long as the sensor output has reached equilibrium with the actual gas concentrations being measured before the measurement is interrupted (e.g., because the sensor is turned off). Typically, faster response is preferred. But a sensor that responds faster is usually more expensive than a slower sensor and sometimes also involves consumables. The ability to also use slower sensors in an inventive sampling system is therefore a big advantage over other metabolic measurement systems.

1 FLOW PROFILES AND PRESSURE IN A VALVELESS, PASSIVE, SIDE-STREAM SAMPLING SYSTEM

A valveless, proportional, passive system produces a flow profile that can be used to make metabolic measurements with a miniaturized mixing chamber. For metabolic measurements, the user simply breathes in and out through the short end of the flow tube into a valveless mixing chamber. Together, the flow tube and the valveless mixing chamber form a passive, proportional, closed-loop metabolic sampling system. As the breath is exhaled, it is compressed while traveling around a 90-degree bend into a vena contracta at the start of the other leg, before expanding back to the original cross-section in the exit diffuser. Upon inhale, the gas travels in the opposite direction, where it is compressed before expanding around the bend back into the original diameter. The asymmetry in design creates conditions where a finite pressure difference between the front of the flow tube, $P_A$, and the vena contracta, $P_C$, on an exhale forces air into the mixing chamber, and the null pressure difference formed on inhale prevents ambient air from entering the mixing chamber with no need for a mechanical valve or moving parts.

Without being bound by any particular theory, the asymmetry between inhale and exhale is a result of non-ideal fluid flow and different dissipation processes for the two flow directions. For an ideal or conservative system, the pressure profile inside the flow tube would be the same for either direction and depend only on the diameter and curvature of the flow tube. For non-dissipative flow, the pressure field is defined by the Bernoulli effect, $$P_1 + \frac{\rho V_1^2}{2} + gh\rho = \text{Constant.} \quad \text{Equation 1}$$

Ignoring minor gravitational effects, the difference in pressure at any two locations is a direct result of the changing speed of the flow. The velocity and pressure drop through a constriction has the same general form, $A_1V_1 = A_2V_2$, where $A_1$ and $A_2$ are the cross sectional area at locations 1 and 2 respectively. The pressure change can solved as $$\Delta P = \frac{\rho}{2} V_1^2 \left(1 + \frac{A_1^2}{A_2^2}\right). \quad \text{Equation 2}$$

For dissipation free flow around a 90-degree bend, the velocity profiles are, $xV_x = RV_R$, where x and R are defined in FIG. 8. The pressure drop across the 45-degree line is $$\Delta P = \frac{D}{r} \rho V^2. \quad \text{Equation 3}$$

These pressure changes are recoverable since, in the construct of the Bernoulli equation, there is no loss mechanism. In real systems, there are dissipative pressure loss events affecting the fluid flow. It is the dissipative effects that create the asymmetry in the flow tube.

The concept of dissipative vs. dynamic pressure change is shown in FIGS. 10A and 10B for an orifice plate in a straight tube. In this example, there are three labeled pressure ports:

a, b, and c, which correspond to $P_A$, $P_C$, and $P_B$ in FIGS. 3A-3D, respectively. In this example, the fluid begins at some arbitrary pressure $P_a$ and velocity $V_a$ on the left hand side before traveling through the constriction at location b and expanding back to the original diameter at location c. As the fluid flows, the pressure and velocity will change to reflect the environment. The pressure decreases inside the constriction, with the reduction in pressure due to loss mechanisms, such as heat, and conversion into kinetic energy as predicted by Equation 3. After exiting the constriction, the diameter of the tube increases to the pre-constriction diameter and roughly speaking the kinetic energy is converted back into pressure. However, much like the path from a to b, some of the energy is lost to heat and $P_c$ is lower than $P_a$ for the dissipative system (second, third, and fifth bars counting from the left of FIG. 10A). When the fluid flow is reversed and $P_c$ is the starting pressure, $P_b$ maintains its low pressure, but $P_a$ is smaller than $P_c$, by the amount indicated by the curve in FIG. 10A. As a result, there is an asymmetry in the differential pressure between $P_a$ and $P_b$, depending on the flow direction. The ideal system with full pressure recovery is shown by the first, fourth, and sixth bars counting from left in FIG. 10A.

The pressure recovery, or the ability of the system to return from pressure $P_b$ to the original pressure ($P_a$ for the left to right direction and $P_c$ for the other) is a measure of the dissipation in the system and is commonly reported as a discharge coefficient ($C_d$). A system with a high discharge coefficient will have a pressure profile resembling the green bars and a low discharge coefficient will be more similar to the red. For a system like the orifice geometry in FIGS. 10A and 10B, locations for a and b and the constriction diameter could be chosen such that the forward flow (a→c) there is a large pressure difference between the a and b locations, $\Delta P_{ab}$. It is this pressure difference that is used to drive the gas into the chamber coupled to the flow tube in FIG. 3A. However, for the opposite flow direction (c→a) the discharge coefficient and gas extraction points can be designed such that there is little or no pressure recovery between b and a, shown in FIG. 10B. This arrangement will create an effective flow diode, where without the need of mechanical valves or pumps. Gas will flow into an auxiliary chamber during exhale and that same chamber will be stagnant on inhale. However, when designing a system for human interaction there are additional concerns beyond proportional sampling and diode behavior related to usability.

2 FLOW DIODES FOR VALVELESS, PASSIVE, SIDE-STREAM SAMPLING

FIGS. 3A and 3B show an inventive passive proportional sampling device, also called a flow tube 300, that samples exhalation (FIG. 3A) but not inhalation (FIG. 3B). The flow tube 300 samples a single direction of an AC gas flow passively, without any moving parts, relying on the direction of flow imparted at the source. More specifically, FIGS. 3A and 3B show a flow tube 300 that passively diverts a proportional amount of exhale into a mixing or measurement chamber (e.g., as shown in FIG. 5C; inserted in between ports 304 and 306) while preventing flow into the same chamber during inhale. The flow direction for inhale and exhale is shown by arrows running along a central conduit or lumen 312 in the shape of a rotated "L" or "J." FIG. 3A shows fluid entering through a first port 302 at the top left, moving around the bend in the lumen 312, and exiting through a second port $P_B$ the bottom. FIG. 3B shows the inhale, with fluid entering through the second port 308 and moving up the flow tube 300 and out the first port 302.

The flow directions in FIGS. 3A and 3B create natural pressure gradients, which are shown by the shading. For the exhale in FIG. 3A, the shape of conduit (lumen 312) causes a large positive pressure to develop at the top of the device, before reaching a minimum pressure around port $P_C$, before regaining some of the lost pressure before the exit at port $P_B$. The inhale starts with a large negative pressure at the human interface (mouthpiece) at the first port 302, but the gas flow starts at the port $P_B$. The gas loses pressure as the cross section of the conduit 312 decreases (indicated by reference numeral 310), until the minimum pressure is achieved near $P_C$. However, with flow in this direction, pressure recovery is discouraged and does not increase back to ambient pressure.

The large pressure difference of about 300 Pa on the exhale flow pattern is used to drive gas between intermediate ports $P_A$ and $P_C$. Since this pressure difference is generated by the flowing fluid, its absolute magnitude is proportional to the flow rate of the fluid. The proportionality in generation and usage is used to collect constant fractions of the total fluid flow. For flow in the other direction, very little pressure difference is generated between $P_A$ and $P_C$, so no gas is pushed between ports $P_A$ and $P_C$. This is represented in the figure by large X's over the ports in FIG. 3B.

FIGS. 3C and 3D show an iteration of an inventive closed-loop sampling system with a symmetric flow tube 301 connected to a valveless mixing chamber 320 during a person's exhalation and inhalation, respectively. It also shows the pressures at ports $P_A$, $P_B$, and $P_C$ during exhalation and inhalation. As the person exhales, the pressure at port $P_A$ is higher than the pressures at ports $P_B$ and $P_C$, as in the bent flow tube 300 in FIGS. 3A and 3B, causing a percentage of the person's breath to flow into the mixing chamber 320, where oxygen and carbon dioxide sensors 322, 324 measure its oxygen and carbon dioxide content, e.g., at a sampling rate of 0.2 Hz to 20 Hz. (The oxygen and carbon dioxide sensors 322, 324 can also be located outside the mixing chamber 320, e.g., in or along the return tubing connecting the output of the mixing chamber 320 to the flow tube 300.) As the person inhales, the pressure at port $P_A$ drops below the pressure at port $P_C$, which remains lower than the pressures at port $P_B$. This pressure differential prevents the gas being inhaled from flowing into the mixing chamber 320 via port $P_B$.

FIGS. 3E and 3F shows the flow tube 300 of FIGS. 3A and 3B with the inhale and exhale ports reversed. Reversing the inhale and exhale ports makes the flow tube suitable for proportionally removing and mixing material from an auxiliary chamber (not shown) coupled to ports $P_A$ and $P_C$ into a single direction of flow path in an AC flow. In this usage of the flow tube, the user exhales through the long straight portion, rather than the short bent portion as in FIGS. 3A and 3B. In this orientation the external chamber (not shown but located between ports $P_A$ and $P_C$) is an extraction chamber rather than a collection chamber. The extraction chamber can be filled with emulsified liquid, saturated vapor, or an agitated and dispersed powder. This material is filtered into the breathing port through $P_C$ during inhale in a measured way.

Much like the device in the breath collection mode, different pressure profiles are developed for the different flow directions. In the exhale direction (FIG. 3E), side-stream ports $P_A$ and $P_C$ have equal pressure, discouraging flow into or out of the extraction chamber. This restricts the loss of the aerosolized material into the local environment.

During an inhale, the pressure gradients should force a known amount of the aerosolized material into the inhale flow stream and to the user. If the density of the aerosolized material in the extraction chamber is known, then the volume of fluid exiting the extraction chamber can be estimated or determined on a breath-by-breath basis.

The ease, passivity, and unidirectional flow of this device allows the user to comfortably inspire the inhalant over the course of many breaths. Additionally, measuring the user's minute volume may enable direct measurement of the inhalant dose. With these combined effects, a lower dose density per breath could be used, easing the aerosol mixing requirements on the inhalant.

3 A BENT OR CURVED FLOW TUBE FOR METABOLIC MEASUREMENT

The flow tube 300 shown in FIGS. 3A and 3B is bent, curved, angled, elbow-shaped, L-shaped, or J-shaped. This shape makes it easier to measure a person's metabolic rate in the field or in a laboratory. The bent flow tube is more stable and comfortable to use due to the reduction in cantilevered mass. And the higher pressure at the outer radius of the bend in the inverted bent flow tube increases the flow to the mixing chamber.

The bent flow tube has a removable, flexible, snorkel-like mouthpiece with bite-wings for comfortable, hands-free use of the flow tube during vigorous physical activities.

The flow tube also has an integrated, transparent saliva trap that prevents the test subject's saliva from dripping out of the flow tube and reduces the likelihood of saliva obstructing the tubes leading the differential pressure pneumotachometer and/or to the tubes leading to (and from) a mixing chamber. Repositioning the tubes leading to the mixing chamber to the upper/distal surface of the bent flow tube also reduces the likelihood of the tubing becoming clogged by saliva.

The bend allows the flow tube to be both wide and long, thereby reducing the torque exerted by the flow tube on the test subject's head and neck without unduly increasing the test subject's respiratory burden. Compared to current devices for measuring metabolic rate, a metabolic cart with a bent flow tube can be smaller, lighter, less expensive, more efficient. In fact, a system with a bent flow tube can be completely passive (i.e., without a pump). As a result, the entire system can be carried by or mounted on the person whose metabolic rate is being measured. And because such a system is reliable and compact, it's possible to use several of them at once (e.g., in a laboratory).

A bent flow tube has a number of advantages over straight flow tubes of similar length. First, the bend reduces the lever arm length of the flow tube when the proximal end is inserted into a test subject's mouth. This makes wearing the flow tube more comfortable for the test subject. It also simplifies the tubing connections between the flow tube and the mixing chamber by eliminating 90-degree bends between the tubing and mouthpiece, e.g., as in FIG. 27 of US Pre-Grant Publication No. 2017/0055875 A1. And it reduces visual obstructions for the test subject and the effects of wind and movement on the metabolic measurements because the distal end faces downward instead of outward.

FIGS. 4A-4J show different views of a high-flow, bent flow tube 100 suitable for measuring a person's metabolic rate in the field or the laboratory. The flow tube 100 comprises a length of tube with a bend 440 between a proximal end 410, or mouthpiece, and a distal end 460. Depending on its curvature, the flow tube 100 may have a maximum inner diameter of 1.1", a minimum inner diameter of 0.32", and a length of 8". It could also have a maximum inner diameter of 1.1", a minimum inner diameter of 0.785", and a length of 7.75". Other dimensions are also possible. Similarly, the bend 140 in FIGS. 4A-4H is about 90 degrees, but bends of other angles (e.g., 75 degrees to 105 degrees) and orientations are also possible. For instance, the flow tube 400 could point sideways or be curved (e.g., in a spiral).

The flow tube 400 defines a lumen 402 that extends from the proximal end 410 to the distal end 460. The lumen's cross section varies along the length of the flow tube 110 as shown in FIG. 4I. The flow tube 400 also defines several ports or openings between its outer surface and the lumen 402, including valve ports 120, a saliva trap connector 430, one or more proportional sampling ports 450, an exit pressure port 452, and an exhale chamber port 454. And it has seats 470 for O-rings at the distal end 460.

The length of the flow tube 400 extending from the bend 440 to the distal end 460 is fixed by the shape of the inner lumen 402. The lumen's diameter is wider at the distal end 460 and the proximal end 410 and narrow at or near the bend 440. The length of the flow tube 400 is usually chosen so that the slope from the lumen's smallest diameter (e.g., the flow constriction 442 shown in FIG. 4I) to its largest diameter at the distal end 460 is about 9° to 10°. This slope is intended to maintain a low expiratory respiratory burden for the test subject.

The portion of the flow tube 400 extending from the bend 440 to the proximal end 460 is long enough to fit the valve ports 420 and the saliva trap port 430 between the proximal end 460 and the bend 440. Valves and a saliva trap (not shown) may be fitted to these ports. The saliva trap and saliva trap port 430 are positioned to prevent the saliva tube from hitting the test subject's chest.

The valves that fit into the valve ports 420 address a technical problem that affects bent flow tubes but not straight flow tubes. Although the J-shape of the flow tube 400 allows for large diameter and long length—and thus a low respiratory burden when exhaling—it increases the respiratory burden when inhaling. The valves near the mouthpiece 410 address this problem by cracking open at low pressure when the test subject inhales. The valves balance or equalize the respiratory burden for inhaling and exhaling. The valves remain close when the test subject exhales, so they don't affect the metabolic measurement.

The saliva trap that fits into the saliva trap port 430 catches saliva excreted by the individual that might otherwise corrupt or interfere with the metabolic measurement. For many test subjects, the mouthpiece triggers salivation. Gravity siphons saliva from the test subject's mouth into the saliva trap via the saliva trap port 430 and a channel or depression 412 (FIG. 4G) in the inner portion of the mouthpiece 410. This prevents the saliva from clogging tubes connected to the mixing chamber ports 450 and keeps the saliva away from clothing.

The mixing chamber ports 450 can be connected to a mixing chamber (FIG. 5C) via respective selective, permeable tubing (FIGS. 4K and 4L). Suitable tubing includes Purma Pure Nafion™ tubing, which is composed of synthetic polymers capable of functioning under relatively high temperatures (e.g., greater than 100° C.) acting as an efficient desiccant of the breath sample, or other tubing composed of ionomers that provide similar material properties to effectively dry the breath sample. If desired, the mixing chamber ports 150 and tubes may be connected using secure Luer lock attachments to reduce the likelihood of unintended tubing disconnections. As the test subject exhales, a portion of the exhaled gas passes through at least one of the mixing chamber ports 450 and corresponding tube to the mixing chamber, where it can be analyzed to determine the test subject's metabolic rate. The exhaled gas is dried as it passes from the flow tube through the Nafion™ tubing to the mixing chamber where $CO_2$ and $O_2$ concentrations are measured. Drying the exhalant is advantageous to gas analysis at the mixing chamber. The exhalant can also be dried with a heater (not shown).

The flow tube 400 can also be connected to a metabolic cart instead of or in addition to the mixing chamber via its distal end 460. The distal end 460 has grooves 470 for O-rings to seal the connection or interface with a tube for the metabolic cart.

As mentioned above, FIGS. 4A-4H show a high-flow, bent-shaped flow tube 400. It is designed for intense exercise, to support peak expiratory flows of around 300 lpm without presenting an objectionable respiratory burden. To support this peak expiratory flow rate, the high-flow, bent-shaped flow tube 400 has a diameter of 0.785". At rest, however, with peak expiratory flows as low as 20-25 lpm, there is insufficient flow resistance (back pressure) to ensure a good sample of the breath. As a result, it works at low flows but just takes a really long time to fill the sample chamber.

FIG. 4J shows a low-flow, bent flow tube 490 designed to ensure good sampling at resting expiratory flows (e.g., 20-25 lpm). It is similar in shape and size to the high-flow, bent flow tube 400 in FIGS. 4A-4H, but has a narrower lumen diameter and is slightly longer. It can be used up to peak values of 80 lpm without saturation. Since the high-flow and low-flow bent flow tubes have an overlapping range, one metabolic measurement protocol is to use the low-flow, bent flow tube 490 for measuring the metabolic rate while the test subject is resting and or doing low-intensity exercise, such as walking, in order to fill the mixing chamber in reasonable time, and to switch to the high-flow, bent flow tube 400 for moderate to intense exercise.

FIGS. 4K and 4L show opposite sides of a bent flow complete with a saliva trap, valves, and tubing that connects to a mixing chamber (see, e.g., FIG. 5C). This tubing is connected to ports PA, PB, and PC as described above. FIG. 4M is a photograph of a bent flow tube with a scuba-style mouthpiece, valves, and a saliva trap. And FIG. 4N shows a bent flow tube whose distal end is connected into a commercial Hans-Rudolph valve, which is what a ParvoMed metabolic cart uses for the subject to breathe into. The skinny tube jutting out of the Hans Rudolph valve is a separate spit trap. In this orientation, the innovative metabolic device can produce concurrent measurements on the same breath data.

4 A PASSIVE, PROPORTIONAL, CLOSED-LOOP SIDE-STREAM SAMPLING WITH A BENT FLOW TUBE AND VALVELESS MIXING CHAMBER

Figure 2:
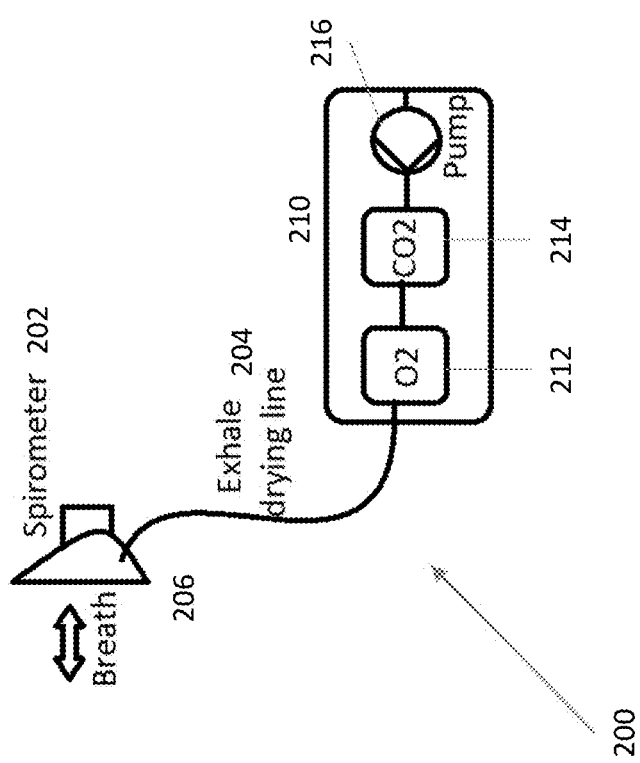
FIG. 2 shows a breath-by-breath indirect calorimeter.

FIG. 5A is a schematic diagram of a proportional sampling system 580. Like the breath-by-breath system 200 shown in FIG. 2, the proportional sampling system 500 in FIG. 5A includes a facemask 586 with a spirometer 582 that measures the volume flow rate of the breath. Inside the breathing mask 586, and before the spirometer 202, a pumping line 584 removes a small continuous sample of gas and transports the sample to a mixing chamber 590. Inside the mixing chamber 590, a pump 596 pulls the breath through an oxygen sensor 592 and a carbon dioxide sensor 594 and deposits it back into the ambient environment One difference between the proportional sampling system 580 shown in FIG. 5A and the breath-by-breath system 200 shown in FIG. 2 is the addition of a feedback signal between the pump 596 and the flow measurement device (spirometer 582). This feedback is represented conceptually by a wire 598 connecting the spirometer 582 and the pump 596 in the FIG. 5A. The feedback signal adjusts the pumping speed of the pump 596 in response to the spirometer measurement. This additional feedback creates a proportional side stream system and avoids the need to rapidly measure and time align gas sample concentrations. Furthermore, the unidirectional nature of the pump 596 eliminates the need for a mechanical valve on the mixing chamber 590 to prevent dilution of the mixing chamber sample during the inhale breath cycle.

The gas exiting the face mask 586 through the exhale drying line 584 is metered by the pump 596 and enters the mixing chamber 590 that houses the sensors 592 and 594. (This is different than the system 200 of FIG. 2, which pulls gas through each of the sensors at a continuous fixed flow rate independent of the breath flow rate.) After the gas enters the mixing chamber 590, it mixes with the gas already present in the mixing chamber 590 before being pushed out by subsequent pump samples.

Proportional pumping enables the use of the mixing chamber 590, similar to the metabolic cart of FIG. 1B, to average several breaths at once. But the proportional sampling and mixing chamber 590 eliminate the time alignment between the gas sensing and flow sensing elements required by a metabolic cart. Furthermore, shutting off the pumping during inhale avoids diluting the gas sample in the mixing chamber with ambient air.

FIG. 5B is a photograph of a passive proportional sampling system 570. It performs like the one in FIG. 5A but is completely passive and does not require the use of an active pump or a mechanical valve on the mixing chamber. The flow tube 300 is the same one shown in FIGS. 3A and 3B and has a bite grip 572 that fits into the intake port for the test subject to stick in his or her mouth and a nose clip 574 to prevent the test subject from breathing in or out through his or her nose. The pressure differences naturally occurring in the flow tube 300 in FIG. 5B act as the pump 596 and the feedback connection 598 in FIG. 5A. The exhale drying line 540 in FIG. 5B is shown as the single-headed arrows leaving the flow tube 300, and the exit port of the pump is represented by the single-headed arrows returning to the flow tube 300. The double-headed arrows in FIG. 5B represent the flow traveling through the spirometer 582.

FIG. 5C shows side view (top) and a rear view (bottom) of the valveless mixing chamber 512 for use in the proportional side-stream sampling system 570 of FIG. 5B. The mixing chamber 512 includes a cavity 511 that receives exhalations from a user via tubing connected to a flow tube (see, e.g., FIGS. 4K and 4L). This tubing may include a proportional sampling tube that delivers a proportional amount of each exhalation to the mixing chamber and a flow return tube that delivers a portion of the mixing chamber's contents to the flow tube. These tubes are connected to ports 513 and 516, respectively, in the rear of the mixing chamber.

The mixing chamber cavity 511 holds one or more sensors (collectively, sensors 520) that measure the volumetric flow rate, the oxygen content, the oxygen partial pressure, the carbon dioxide content, the carbon dioxide partial pressure, etc. These sensors may include, but are not limited to, an oxygen sensor 520a and a carbon dioxide sensor 520b. It also has ports for high-pressure and low-pressure measurements in the exhale direction. The sensors can be mounted on an electronics board 522 (e.g., a printed circuit board) and powered by batteries 524 or another suitable power supply as shown in FIG. 5C. The mixing chamber cavity 511 is small in size (interior volume, which may be about 1 BEV to about 20 BEVs (500 ccs to 10,000 ccs)) to allow rapid filling during rest and activity as a factor of individual lung capacity.

FIG. 5D illustrates a closed-loop, passive, proportional side-stream sampling system 500 with the bent flow tube 400 of FIGS. 4A-4I and a valved mixing chamber 510 to prevent dilution of the gas sample contained in the chamber during inhalation. The inlet of the bent flow tube 400 fits into the mouth of a person 501, possibly with a mouthpiece for a better fit/seal. As the person breathes out, most of the exhalation 503 travels through the flow tube 400 to the outlet. A constriction 442 in the flow tube 400 creates a pressure gradient that forces a proportional amount 505 of the exhalation out of the exhale pressure port 454. This proportional amount 505 travels through tubing 540 to the mixing chamber 510.

The proportional amount 505 mixes with fractions of the user's earlier breaths in the mixing chamber 510. At the same time, one or more sensors 520 in the mixing chamber 510 measure the partial pressures of oxygen, carbon dioxide, etc. in the mixing chamber 510. When the pressure in the mixing chamber 530 reaches a threshold, excess gas vents out of the valved mixing chamber 510 via a check valve 530 that prevents gas from entering the mixing chamber 510 when an individual 501 inhales.

FIG. 5E illustrates the open-loop, passive, proportional side-stream sampling system 570 of FIG. 5B with the bent flow tube 400 of FIGS. 4A-4I and a valveless mixing chamber 512. Again, the inlet of the bent flow tube 400 fits into the mouth of a person 501, possibly with a mouthpiece for a better fit/seal. As the person breathes out, most of the exhalation 503 travels through the flow tube 400 to the outlet. A constriction 442 in the flow tube 400 creates a pressure gradient that forces a proportional amount 505 of the exhalation out of the exhale pressure port 454. This proportional amount 505 travels through tubing 540 to the valveless mixing chamber 512.

Again, the proportional amount 505 mixes with fractions of the user's earlier breaths in the valveless mixing chamber 512. At the same time, one or more sensors 520 in the mixing chamber 512 measure the partial pressures of oxygen, carbon dioxide, etc. in the mixing chamber 512. Excess gas travels out of the mixing chamber 512 to the port $P_C$ of the bent flow tube 400 via a return tubing 542. The sensors 520 can also be located in or in fluid communication with the return tubing 542 instead of in the valveless mixing chamber 512. The sensors 520 can even be located at or just before port $P_C$ of the bent flow tube 400.

FIG. 5F is a photograph of the open-loop, passive, proportional side-stream sampling system 570 with the bent flow tube 400 in operation with the valveless mixing chamber 512. A plastic tube in the test subject's mouth fits over the proximal end of the flow tube. If desired, this plastic tube may be replaced with a scuba-style bite mouthpiece (e.g., bite grip 572 in FIG. 5B) fitted into the proximal end 410 as shown in FIG. 4M to create a better seal between the test subject's mouth and the flow tube 400 and to make the flow tube 410 more comfortable for the test subject.

With proximal end 410 properly in place, the bend 440 causes the distal end 460 of the flow tube 400 to point down or at an angle. Because the flow tube 400 bends down, it doesn't extend as far out of the test subject's mouth. Thus, compared to a straight flow tube with the same length, the bent flow tube 400 has a shorter lever arm length, reducing the torque that it exerts on the test subject's jaw, head, and neck.

5 RESPIRATORY BURDEN

Respiratory burden is a physiological measure of difficulty associated with the mechanics of breathing. This is a pressure difference between the gas as it is exhaled by the subject and that of the ambient environment. In FIG. 10A, this is the difference between the pressure at point a and c, $\Delta P_{ac}$ and it is labeled net pressure loss in FIG. 10B. If the loss mechanisms are too high in a sampling device, the user must breathe more forcefully and perhaps more rapidly than would otherwise be required. Too high a respiratory burden triggers an uncomfortable sense of not getting sufficient oxygen to sustain the level of metabolic effort. For comfortable use, the respiratory burden through the whole measurement system should be less than ~2" $H_2O$. For a metabolic device that is designed to work in many conditions, from resting (peak flow rates of 15 L/min) to high-intensity exercise, such as running (peak flow rates of ~400 L/min), care should be taken to ensure that the burden is not too high. This contradicts with the goal of pressure generated collection, where larger pressure drops send more gas into the mixing chamber.

The pressure loss and velocity fields of a flow as it passes through various geometries are well-studied. For instance, laminar pressure head loss at low Reynolds number is $\propto \dot{V}$ and pressure loss due to turbulent flow is $\propto \dot{V}^2$. Many systems contain some combination of the two effects, which are represented by the discharge coefficient and pressure recovery. FIG. 11 shows the pressure recovery in a straight wall diffuser as a function of the expansion angle. FIG. 12 shows several different diffuser flow regimes, catalogued by the appearance of eddies in the stream. The different eddy formations are responsible the changing pressure recovery shown in FIG. 11. A subset of the flow regimes is defined by the diffuser geometry in FIG. 13. All of these data are combined to intuitively understand how to construct a proportional sampling device. With increasing diffuser angles, more flow separates from the wall to produce back pressure and irrecoverable pressure/energy loss. Using the pressure loss coefficient for a diffuser in FIG. 11 as a reference, a gentle expansion at 9-10 degrees should work as an efficient diffuser for poor pressure recovery, the extreme angle of 90 degrees, or an orifice plate, would create total flow separation as is seen in FIG. 10.

For compression, the flow tube or nozzle also should not contain a large dissipation since it will contribute to inhale pressure burden. For a nozzle, the discharge coefficient has been measured to be very near unity and nearly independent of angle or shape, as shown in FIG. 14.

A venturi tube is a geometry that contains both a nozzle to compress the gas and a diffuser to expand it. FIGS. 3A and 3B show examples of venturi tubes with approximately 90-degree bends. In a flow diode, flow in the ab (exhale) direction should have a different characteristic than flow in ba (inhale) direction. Specifically, when gas flows from b to a, the pressure recovery should be strongly suppressed. While flow in the ab direction, recovery is encouraged. The diffuser angle for flow in the ba direction should be either large or very shallow as in FIG. 11. Large was selected for usability and length. For the exhale flow, the permanent pressure drops for the nozzle direction, ab, will be modest as nozzles have a very mild effect on permanent pressure losses.

FIG. 15 shows the pressure recovery as a function of β, where β is the ratio of the minimum tube diameter to its maximum for an orifice plate. This is the extreme case diffuser, with an equivalent to 90-degree angle. An orifice opening creates a jet flow pattern, FIG. 12. For small β, less than 10% of the minimum pressure is recovered. As β increases, so does the pressure recovery, causing a reduction in respiratory burden. Conceptually, this shows that for small β a straight venturi tube with a very sharp nozzle entrance and a gradual diffuser exit can work as an effective fluid dynamic flow diode. FIG. 16 shows one such design where the diffuser and nozzle angles are chosen to produce a diode flow effect. The fact that this effect can be found in many different geometries indicates that the chosen bent venturi is just one of many possible designs.

For a general flow diode design, location of ports a and b (e.g., FIG. 10) can be tuned for a more effective pressure cancelation, with possible side effect of a reduction in driving pressure during exhale. As the flow impedance decreases, causing a drop in the gas driving pressure, the locations of ports a and b should be located more precisely and likely closer together, which could decrease the collection percent during exhale. For low exhale volumetric flow rates associated with resting or walking conditions, breathing through a high impedance breathing tube is not arduous, but as activity level increases and more air is needed by the subject, a less restrictive system is required (larger β for the orifice example).

This becomes a problem when respiratory burden is considered. For low flow rates associated with resting or walking conditions, pushing air through a small tube is not arduous, but as activity level increases, the minimum diameter of the device should also increase. The total pressure head loss for this device is calculated by taking the difference between the starting pressure at the mouth interface and the ending pressure where the exhaled breath rejoins the ambient environment. In particular, a small constriction is impractical for comfortable use in an exercise setting, as shown in FIG. 17. For this particular flow tube, the comfortable respiratory burden is exceeded at a nominal flow rate of about 100 L/min. A balance between reducing or minimizing respiratory burden for the user and increasing or maximizing the driving pressure ($P_B-P_A$) to deliver exhaled gas to the mixing chamber should be specifically designed to span the anticipated physiological range.

Possibilities for expanding the physiological range for this type of device include: creating many different flow tubes (calibrated to specific individuals or physiological ranges), moving the pressure port to idealized locations for different uses (accept the trade of low collection rate for efficient diode behavior), or adding additional structure to the flow tube to change the pressure recovery diagram (as was done by adding the 90 degree turn to the venturi structure). Each of these solutions has drawbacks: producing many flow tubes, e.g., one for resting, walking, jogging, running, small people, large people, male, female, and so on becomes cumbersome. Adjusting the port locations to optimize one effect, like the diode flow effect, can affect other properties of the flow tube, such as increasing or maximizing the gas collection percentage. Often the design parameters oppose each other, so achieving the minimum inhale pressure differential comes at a cost imposed on the gas collection rate. So, while better pressure matching may be produced for the inhale, less driving pressure is developed on exhale. This slows down the collection of gas into the mixing chamber, increasing the time scale for measurement and reducing the achievable temporal resolution of changes in physiology. Optimizing the interior geometry makes the design more complicated, involves additional engineering resources, and increases the difficulty of analytic calculation.

One possible improvement to an orifice plate or venturi design is explored. This is to combine different flow processes; place a 90-degree turn along the path of a standard venturi, as shown in FIGS. 3A and 3B. In this design, the flow tube bent intersects the inhale diffuser, drastically changing the inhale pressure recovery. However, as is shown in FIG. 14, the curvature of the nozzle has little effect on the pressure drop for flow in that direction. The flow through a curved nozzle and curved diffuser are examined, starting with the exhale flow direction. As gas is pushed out of the individual and into the flow tube it is compressed through a nozzle while going around a corner. In this situation, the pressure change is mainly due to the idealized Bernoulli Effect, where pressure is converted into kinetic energy, with little influence from the nozzle. This is due to a nozzle's efficiency's relative indifference to flow conditions.

For gas flow in the opposite direction, the gas is expanded around the curve, rather than contracted. Curved diffusers still have the standard Bernoulli pressure change moving out of the vena contracta, but diffuser pressure recovery has been shown to be sensitive to area ratios, divergence angles, and profile turning angles. These different effects have been shown to alter the flow rates for switching between the different flow profiles shown in FIG. 12 and help drive the pressure difference between $P_C$ and $P_A$ toward zero during an inhale. For a bend angle of 90 degrees, a diffuser angle of 10 degrees or larger may produce a fully developed stall and have very poor recovery. Therefore, even for low impedance devices, or flow tubes designed for exercise, the inhale recovery may be very modest and the difference between $P_C$ and $P_A$ will be small.

Integrating a bend (e.g., of 75-105 degrees) into the front end of the flow tube is just one enhancing geometric effect that could be used, and the only one explored. With this design, a range of flow rates from 5 L/min to 400 L/min can be spanned with 2 flow tubes, while keeping the respiratory burden under 2" of water on exhale. Since exhaling involves less muscle effort than inhaling, these auxiliary inhale valves help balance the inhale/exhale effort and make the tube easier to breathe through, without affecting collection of the breath during exhale. Additionally, the inhale breath flow rate is not used in metabolic analysis, so no inhale data needs to be collected. For the aerosol application, exhale valves could be incorporated, while not affecting the medicine delivery.

Designing the pressure between $P_A$ and $P_C$ to equal zero over the whole flow range is extremely sensitive, so additional measures are taken to mitigate the collection of gas upon an inhale. Since b is located at the vena contracta, which is theoretically the lowest pressure position in the system, independent of flow direction, gas flow into the mixing chamber should always travel from $P_C$ to $P_A$, and not in the opposite direction. A result of this one-way flow is the angle of the gas connections to $P_A$ and $P_C$ can be aligned with the exhale breath streamlines and counter aligned to the inhale flow direction. FIG. 18 shows this diagrammatically. As shown in the schematic, during an exhale the gas entering the main stream flow from the collection volume has the same flow direction. Therefore, the two should mix with little obstruction. However, during inhale (FIG. 18B), the flow direction through the sample chamber is opposite the inhale flow direction. The opposing flow creates an eddy that discourages further flow in that direction, similar to a Tesla valve, shown in FIG. 18C. Therefore, the angles of these ports deter gas flow, increasing the efficacy of the flow diode. With an effective flow diode, one-half of the passive gas-sampling problem—avoiding passive sample dilution—is solved, leaving the proportional gas sampling unresolved. Proportional gas sampling is shown mathematically by:

$$\frac{\dot{V}_{main}}{\dot{V}_{Collection}} = \text{constant} \qquad \text{Equation 4}$$

The main flow through the venturi constriction on exhale has the pressure relation shown in Equation 2. Equation 5 is the functional fit flow data shown in FIG. 17.

$$\Delta P_{ac} \sim a\dot{V}_{MF}^2 + b\dot{V}_{MF}. \qquad \text{Equation 5}$$

The linear term here represents the lost energy due to laminar losses and the square term is a combination of turbulent losses and the Venturi pressure effects. This same pressure difference appearing in this equation is used to drive the flow through the ports a and c into the mixing chamber. Flow through the conduit and into the mixing chamber has a pressure relationship of Equation 6:

$$\Delta P_{ac} \sim a'\dot{V}_{MC}^2 + b'\dot{V}_{MC}. \qquad \text{Equation 6}$$

where once again, a' is a measure of the permanent pressure loss due to turbulence and b' is a measure of the laminar flow losses. For the side stream flow, there are no Venturi effects since the input and output ports have the same cross section, therefore all of the pressure changes are due to losses. Since the pressure drops in equations 5 and 6 are the same, $$\frac{\dot{V}_{MC}}{\dot{V}_{MF}} = \gamma$$

is only true when $a = \gamma^2$ a' and $b = \gamma b'$ or approximately true when $a \gg b$ and $a' \gg b'$ or $a \ll b$ and $a' \ll b'$. In the special cases of dominant linear or quadratic terms, the volumetric flow ratio simplifies to a simple ratio of either laminar or turbulent. Generally speaking, $\gamma$ is less than one for our application which implies that the laminar component of the loss for the mixing chamber flow should be relatively larger than for the main flow path. Therefore, the side stream connections should be longer and narrower to maintain proportionality.

FIG. 19 shows the measured mixing chamber collection ratio for both inhale and exhale for the low flow version of the flow tube and FIG. 20 shows the same information for the high flow. In this figure, the y-axis is the collection percent and the x-axis shows the mean flow rate pushed through the main flow tube path.

As a further demonstration of the efficacy of this design, FIG. 21 shows the pressure $\Delta P_{ab}$ for several breathing cycles as a function of time. The exhale is clearly distinguished from the inhale by the large pressure changes seen on exhale and small pressure differences on inhale.

The relationship between $\dot{V}_{MC}$ and $\dot{V}_{MF}$ can be used to simplify the measurement of $\dot{V}_{MF}$. Typical metabolic devices decouple the gas collection and flow measurement into two separate measurements. The proportional sampling technique described here allows these two processes to be conducted on the same gas flow. Since $\Delta P_{ac}$ describes both the collection pressure drop and the main flow through the flow tube, one measurement describes both flow rates simultaneously. This enables the auxiliary chamber pressure drop measurement to be used as the flow measurement for the flow tube. This innovation has three distinct advantages: 1. There are fewer connections between the flow tube and the mixing chamber as the gas transport and flow are measured concurrently. 2. The measurement pressure $\Delta P_{ac}$ is measured in the mixing chamber, at the end of a long narrow conduit. Measuring pressure differential of a laminar flow is much more stable and has fewer pressure and velocity fluctuations. This increases the fidelity of the pressure measurement and allows it to be made in the controlled mixing chamber environment. 3. The pressure measurement is made in a tube where there is regular gas flow. Gas flow through the pressure measurement ports decreases the likelihood of water or saliva capillary condensing in the measurement port.

6 BREATH DYNAMICS

A deconstruction of a breath cycle is shown in FIG. 6. The representative breathing cycles show the dynamic gas measurements (% $CO_2$ and % $O_2$) with the bottom and middle curves and the flow rate measurement in the upper portion of the plot. For convenience of description, the breath cycle shown in FIG. 4 is broken up into three distinct components; inhale, dead space exhale, and alveolar exhale breath phase. The left and right axes divide the plot into two sections: the left describes the gas concentration change and the right displays the changing volumetric flow rates. The bottom axis is a shared time for both sets of curves.

The inhale, dead space, and alveolar components have different dynamic relationships between the gas concentration and the flow rate. Two of them are simple because of a constant gas concentration. For inhale, the gas concentration is equal to the ambient environment (nominally 20.94% $O_2$ and 0.04% $CO_2$ for dry air with the concentrations reduced to account for non-zero relative humidity) flowing into the individual at inhale. Since the gas concentration is constant over the inhale (with the possible exception of a small amount of residual end-tidal alveolar gas left in the flow tube from the previous exhale breath), an integral of the flow rate determines the tidal volume, $VO_2$, $VCO_2$, and $VH_2O$. The majority of the exhale varies in both gas concentration and flow rate. The exhale can be broken into two components: the dead space (the volume of inhaled air in the mouth and esophagus that does not participate in gaseous exchange with the lungs) and the alveolar gas, the former has a nearly constant gas concentration (apart from changes in humidity) and the latter in which both the gas concentrations and flow rate vary with time.

The dead space portion is the first part of the exhale to emerge from the individual and it contains the gas stored in the mouth, esophagus, and metabolic measuring device. The gas concentrations in this section of breath have a change in gas humidity from the subject, but the dry concentration changes in the dead space are much smaller than the alveolar portion of the breath. The dead space breath typically results in the highest volumetric flow rates as the lungs are contracting rapidly from full expansion. The dead space air is either at atmospheric gas concentrations or a humidified version of ambient condition, since it did not enter the lungs for alveolar exchange. The second phase of the exhale begins, without pause, following the dead space gas. This is the most complicated portion of the breath to measure as it has both a variable flow rate and variable constituent gas concentrations.

In comparison to the inhale, where a single measurement of ambient gas concentration and a measurement of the volume flow rate characterizes the entire inhale, the exhale breath where the flow is more rapid. The inhaled and exhaled volumes are assumed to be known precisely, so no Haldane or other volume correction factors are applied and the differences between the two collection systems are due to the measurement bias introduced by a constant-rate sampling pump.

|  | Total Volume | $VO_2$ | $VCO_2$ | $O_2$ % | $CO_2$ % | EE |
|---|---|---|---|---|---|---|
| Whole Breath 1 | 2.14 L | 0.13 L | 0.10 L | 6.11% | 4.57% | 1.59 |
| Whole Breath 2 | 2.23 L | 0.14 L | 0.10 L | 6.25% | 4.68% | 1.69 |
| Constant Rate 1 | 32.8 cc | 2.06 cc | 1.55 cc | 6.58% | 4.93% | 1.71 |
| Constant Rate 2 | 34.4 cc | 2.16 cc | 1.62 cc | 6.28% | 4.73% | 1.70 |
| Proportional 1 | 17.1 cc | 1.05 cc | 0.78 cc | 6.11% | 4.57% | 1.59 |
| Proportional 2 | 17.8 cc | 1.11 cc | 0.84 cc | 6.25% | 4.68% | 1.69 | is dynamic, and includes changes to both the gas concentration and flow rate. Therefore, to compute relevant metabolic measures both flow rate and concentration change have to be known and are functions of time. Knowledge of the full temporal relationship for flow rate and gas concentration is used to calculate the integral of their product. The synchronization and balance of flow and gas concentration measurements is the reason why metabolic carts collect whole breaths in a mixing chamber. When the whole breath is collected, the gas contained in the whole breath is naturally volume averaged before being extracted by the gas sensors. With an averaged sample, the volume integrals can be calculated with standard flow integrals to produce the metabolic variables. Breath-by-breath measurement systems don't average the data and need to have time-synchronized high-rate measurements of both the volumetric flow and the associated gas concentrations to directly calculate and measure the metabolic quantities.

FIGS. 7A and 7B shows the differential volume elements from the breaths in FIG. 6. FIGS. 7A and 7B differentiate between two different sampling methods, one that has a constant volumetric pumping rate (FIG. 7A) and the one which varies the volumetric pumping rate in proportion to the exhale flow rate (FIG. 7B). The differential volume elements of FIGS. 7A and 7B are separated into smaller components, indicating the volume fractions of $O_2$, $CO_2$, or inert (largely $N_2$) gas. The total volume and fractional gas volumes for these data are integrated and summarized in Table 1 (below).

These example data show the distinction between proportional sampling of the exhaled breath versus a constant-rate sampling technique, as would occur with a system without feedback. For this experiment, the pump rate for the constant-rate sampling system is 50 cc/min and the proportional pumping system removes 2% of gas from each breath relative to the flow rate. Summing the three differential volume elements together over the whole breath delivers the tidal volume and summing specific components will give the gas volumes.

For the constant-rate pumped system, each bar represents a differential volume element in the plot of FIG. 7A. Each bar in FIG. 7A is the same since the volume elements are being collected at a constant rate regardless of the exhale flow rate. In contrast, the volume bars for the proportional system track the shape of the exhale flow rate (FIG. 7B). FIGS. 7A and 7B show that the continuous pumping method gives a higher than deserved weight to the volumetric gas measurements corresponding to the parts of the respiration cycle where the flow is slower and less weight than deserved to the volumetric gas concentrations in the regions of the The first two rows of data in Table 1 are equivalent to a Douglas bag measurement where the whole breath volume is captured. These rows represent a ground truth against which to compare the constant-rate and proportional sampling measurement techniques. The total volume column of the table shows the advantage of side-stream sampling techniques over the traditional systems. The side-stream systems collect only a fraction of the gas relative the Douglas bag technique. The volumes of the two side stream techniques are not equivalent in this experiment, but the pump rates and collection percent were arbitrarily chosen and could be scaled up or down to match.

Table 1 displays a fundamental difference between the exhale collection by a proportionally pumped system compared to a constant-rate pump system. With a constant pump rate, the dynamic relationship of the gas concentration with respect to the exhale flow rate is lost and the measured concentrations of $O_2$ and $CO_2$ become biased. For the constant flow rate, the collected volume element of end tidal gas has the same size as the volume element from the initial dead space despite their different instantaneous exhale flow rates leading to a measured concentration of 6.58 and 6.28 for $O_2$ and 4.93 and 4.73 for $CO_2$, rather than the exhaled 6.11, 6.25, 4.57, and 4.68 gas percentages. The error in energy expenditure (EE) calculated scales directly with the gas percentage error and is inconsistent between the different breaths. In the first breath the constant rate sampling produces nearly a 10% error, while in the second breath the error is hardly present at all. In the proportional system, the gas concentration percentages are preserved since the differential volume elements scale directly with the flow rate. Not scaling the gas collection will not only give incorrect answers for single breaths, it will also skew the intrabreath $VO_2$ and $VCO_2$ concentrations, as is shown in Table 1.

Further, if consecutive breaths have different tidal volumes, but the same respiration rate, a constantly pumped system may average the two breaths as equals when in reality the physiological effects of the consecutive breaths could be quite different.

This error introduced by constant-rate sampling varies across individuals, situation, or experiment. For the case of a large, long, slow breath, a constant pumping rate may spend a relatively long time pumping the low flow rate end of the breath compared to the high flow rate beginning of a breath. The resulting breath sample will may produce average concentration values skewed towards the end tidal measurements, rather than a realistic balance of dead space and end tidal. However, if a test individual has shorter breaths, with a more consistent flow rate, this systematic error in the data could disappear altogether.

FIG. 6 shows two breath exhale cycles and identifies the epochs comprising a typical breath cycle as well as the parameters of interest. For metabolic measurements, these parameters include $O_2$ percentage, $CO_2$ percentage, and gas volume. The volumetric flow rate is shown as the upper trace with scale values displayed on the right-hand axis. The breath shown starts in the middle of an inhale with a flow rate of about −100 L/min before the subject initiates an exhale starting at around 0.5 seconds. The gas concentrations for $O_2$ and $CO_2$ are represented by the upper and lower traces, respectively. The numbers shown for gas concentrations displayed are $CO_2$ produced and $O_2$ consumed. The breaths are broken up into four distinct time regions based on their behavior: dead space, main exhale, end tidal, and inhale.

FIGS. 7A and 7B are bar charts showing the gas collection differential volume elements (DVEs) for two different pumping methods. The top bar chart shows the DVEs for a constant pump rate system (e.g., a conventional breath-by-breath system). The constant pump rate is indicated by the equal heights of all of the DVEs. The bottom bar chart has a pump rate that is scaled proportionally by the volume flow rate. This is indicated by the varying heights of all of the DVEs. These data were both extracted from the breathing data shown in FIG. 6. The upper bars are the DVE of inert gas entering the mixing chamber, the middle bars are $CO_2$, and the lower bars are $O_2$. The relative contribution of each DVE to the end tidal volume, $VO_2$, and $VCO_2$ for each bar is represented by the bar height.

FIG. 8 shows the velocity fields and pressure generated for a nearly dissipation-free flow around a 90-degree bend, e.g., as in the flow tube of FIGS. 3A and 3B. The radial vectors R and X are shown by the arrows extending diagonally from lower right to upper left. The vector R goes to the outer most area of the fluid flow and the vector X ranges through the flow zone. The relative pressure differences are shown in the legend with larger pressures at the outside of the bend and smaller pressures at the inside of the bend. The arrows in the bend show the flow velocity field.

FIG. 9 shows the velocity fields and pressure generated for a nearly dissipation-free flow through a restriction. The relative pressure differences are shown in the same shading as FIG. 8, with larger pressures at the left and right ends and smaller pressures in the middle. The arrows show the flow velocity field. There is no loss in pressure in FIG. 9, so the pressure fully recovers.

FIG. 10A shows a diagram of an orifice plate placed in a horizontal fluid flow from left to right through a conduit or lumen. The dashed lines represent the streamlines of the fluid flow. In FIG. 10A, the fluid is squeezed through a small orifice and naturally returns back to its original diameter. The curve shows the typical pressure change as a function of distance in the horizontal direction. The pressure is largest before entering the constriction, before reaching its minimum at the Vena contracta. The pressure recovers some of its original value further down the tube. The permanent pressure losses are marked, as well as the maximum pressure difference. The recoverable pressure change is the difference between the pressures located at points b and c.

The bar plots above the conduit show the difference between the pressure change for a dissipation-free system and one that includes dissipation. Both flow types start at the same pressure before reducing their pressure immediately after the orifice. In FIG. 10A, the pressure drops between points a and b are the same for both flow types, but this isn't necessarily the case in general. The dissipation-free system recovers all of its original pressure by the time it reaches point c, while the system which includes dissipation does not.

FIG. 10B is a more detailed plot of the pressure change through an orifice plate. The locations A and B from FIG. 10A are shown for this geometry. For flow from the left to right, a large pressure difference is present between the two points, but for flow in the other direction the difference in pressure between these two points is more modest.

FIG. 11 is a plot of pressure lost for a cone-shaped diffuser as a function of the diffuser cone divergence angle. There is a minimum in pressure loss at a cone divergence angle of around 9 or 10 degrees, and the pressure loss is greater on either side of the inflection point.

FIG. 12 shows the different levels of stall in flow through a diffuser. These flow patterns are responsible for variations in pressure recovery.

FIG. 13 is a plot of diffuser angle versus normalized length for conical diffusers (e.g., as in the flow tube of FIGS. 3A and 3B) and two-dimensional diffusers. Appreciable stall occurs at upper right, and there is no appreciable stall at lower left. Without being bound by any particular theory, this shows that the appearance of eddies, energy loss, and stall is a function of both the diffuser angle and the length of the diffuser. The goal is to produce a flow tube that has no appreciable stall for directions with good pressure recovery and to increase or maximize the stall for flow in directions where poor pressure recovery is desired.

FIG. 14 is a plot showing the stability of the discharge coefficient for nozzles of differing geometries. As opposed to a diffuser, the nozzle is fairly insensitive to geometry (e.g., nozzle angle, bending tube, etc.) it can be used to help create biased flow patterns.

FIG. 15 is a plot showing the pressure recovery from the minimum pressure point in for flow through an orifice. Orifice flow can be considered flow through a hole in a wall. Without being bound by any particular theory, FIG. 15 shows that the pressure recovery is dependent on Beta, or the ratio of the minimum flow diameter and main flow diameter. Since the pressure reaches a minimum, there exists a pair of points for all Beta where the absolute pressure is the same for two points on either side of the minimum. This suggests an orifice geometry can be used to create a perfect flow diode, independent of flow rate. This is because when two different points are in a pressure equilibrium there is no driving force to promote flow between them. This information can be used to choose the chamber pick-off points (i.e., the locations of ports $P_A$ and $P_C$) in flow tubes similar to FIG. 3A, 3B, 3E, 3F, 16A, or 16B.

FIGS. 16A and 16B shows SolidWorks™ simulations of the pressure and velocity fields inside of an asymmetric constriction geometry for flow in opposite directions (down in FIG. 16A and up in FIG. 16B). The relative pressure is the same scale for both directions and is shaded according to the shading bars. The arrows represent the velocity field vectors and in both cases flow separation, as shown in FIG. 12, is seen by circularity in the velocity. The flow direction with larger flow separation has a poorer pressure recovery than the alternate direction, suggesting that an optimized straight device like this one could also work as a passive flow tube like the ones shown in FIGS. 3A-3F. For the example, the tube shown in FIGS. 16A and 16B could be modified for passive side stream sampling by adding gas collection side stream ports at the top of the narrow neck and the bottom of the tube, labeled $P_A$ and $P_C$ in the drawing.

FIG. 17 is a plot of the measured gas flow rate as a function of pressure differential across the flow tube for a generic sensor. This data is extracted from a low-flow, or resting, sensor since just 100 L/min produces a pressure drop of 2"/H$_2$O. The relationship between flow induced pressure change and flow rate is quadratic, independent of its source (dissipative or not). The flow rate entering the mixing chamber of FIG. 5B will have a functionally comparable pressure drop as the data in FIG. 17, but the flow rates should be reduced by roughly a factor of 50. The proportionality of the flow rate into the mixing chamber to the flow rate through the flow tube implies that a differential pressure measurement can also be made at the point where the sample and return tubes enter and exit the mixing chamber, thereby eliminating the need for additional pressure tubes attached to the flow tube. In other words, measurement of the flow into and out of the mixing chamber can be used as a proxy measurement of flow through the flow tube.

FIGS. 18A and 18B shows a secondary method of reducing the amount of flow into the auxiliary chamber when the flow tube is used as a collection device. When the flow tube is used for extraction the same principles hold, but inhale and exhale are reversed. The main gas flow is indicated by large arrows and the flow into and out of the collection chamber is indicated by smaller arrows. When the velocity vectors of both fields are lined up at the entrance and exit ports, fluid is free to flow into the collection chamber. But when the flow vectors of the two different flow paths are in opposition, additional flow stagnation is encountered and flow along the auxiliary path is further suppressed.

FIG. 18C shows a design for a Tesla flow diode which uses the principle illustrated in FIGS. 18A and 18B to create mono-directional flow. In the Tesla diode, the reverse direction flow is created by the fluids preference to follow the wall contour of its conduit. But the conflicting flow direction principle is the same.

FIG. 19 is a plot showing the effectiveness of the proportional sampling technique for three different high-flow flow tubes like the one in FIGS. 3A and 3B. The data were collected over a wide variety of tidal volumes and average flowrates. The x-axis is the mean flow rate over the course of a single breath. Negative flow rates represent inhale flow and positive flow rates are for exhale flows. The y-axis is the ratio of the amount of gas collected in the mixing chamber to the amount of gas that passes through the flow tube, divided by 100. A value of 100% on the y-axis indicates that all of the exhale traveled into the mixing chamber, which is the standard for metabolic carts. For an ideal passive sidestream sampling system, the collection percent for exhale is a constant number representing an exact proportional sampling and the inhale collection is zero.

FIG. 20 shows the same data set as FIG. 19, but for a flow tube like the one in FIGS. 3A and 3B with a higher respiratory burden. The gain with the higher burden is an increase in the collection percent from about 0.8% to 2%, allowing the collection chamber to fill more rapidly with exhaled breath during use.

FIG. 21 shows the raw data used to estimate or determine the volume of exhale/inhale entering the collection chamber in the passive side stream sampling system of FIG. 5B. The x-axis is time in seconds and the y-axis is the differential pressure between ports PA and PC from FIGS. 3A and 3B. Larger differential pressures represent larger flow rates of gas entering the mixing chamber as in FIG. 17.

FIG. 21 shows that the flow rate of gas entering the chamber varies over many breathing cycles, starting from rapid flow at the beginning to slower flow by the end. The raw data shown here displays the difference in pressures generated in the two flow directions. Each cycle has an inhale and an exhale. For this device, each inhale has a negative differential pressure and the exhale is positive.

FIG. 22 is a close-up of a few breathing cycles from FIG. 21. When the time axis is expanded, it is much easier to see the difference between an inhale and an exhale. The horizontal and vertical axes show time in seconds and differential pressure in Pa, respectively.

FIG. 23A is a cross-sectional view of a mixing chamber 2312 with a perforated baffle 2326 and a perforated circuit board or panel 2322 disposed therein. FIG. 23B is a top, cut-away view of the mixing chamber 2312 and perforated circuit board 2322 shown in FIG. 23A. The perforated baffle 2326 and perforated circuit board 2322 provide a low resistance path for gas flow and aid in mixing the expired boluses of gas before same arrive at gas sensor(s) 2320 (e.g., oxygen and/or carbon dioxide sensors). Put differently, the perforations in the perforated baffle 2326 and perforated circuit board 2322 foster mixing of multiple breath fractions. This or a similar arrangement provides a low resistance path for gas flow while ensuring each incoming breath mixes with the residual from previous breaths, forming a volumetric average with the previous few exhaled breaths.

7 CONCLUSION

In conclusion, a compact accurate metabolic device with the same fidelity of larger metabolic carts is disclosed. It can passively collect exhaled breath at a collection rate that is directly proportional to the exhale flow rate to produce a control volume of gas with exactly the same volume concentration percentages as a Douglas bag collection of the entire breath. The values of VO$_2$, VCO$_2$, and minute ventilation can be used to calculate energy expenditure and respiratory exchange ratio, among other variables, in a package that is portable and unobtrusive to the user. In particular, because the flow tube is passive—it has no moving parts or electronics—it can be disconnected from the mixing chamber and sanitized between uses by soaking in disinfectant. The lack of moving parts also reduces manufacturing cost and increases service life. This system alleviates the requirement of fast sensors and complicated calibration procedures common to mobile breath-by breath systems, enabling for a low-cost, personal-use sensor. It can make on-demand measurements of respiratory exchange ratio, VO$_2$, tidal volume, minute volume energy expenditure, and other metrics related to metabolic health and performance with supporting system software.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A flow-rate proportional passive side-stream sampling system comprising:
    a bent flow tube, defining an inner lumen extending from an inlet of the bent flow tube to an outlet of the bent flow tube, the bent flow tube having a bend between the inlet and the outlet, the bent flow tube configured to receive an exhaled breath from a person at the inlet, convey the exhaled breath from the inlet to the outlet via the bent flow tube, and convey an inhalation from the outlet to the inlet and to the person via the bent flow tube;
    a first port disposed on the bent flow tube between the inlet of the bent flow tube and the bend and in fluid communication with the inner lumen;
    a mixing chamber, in fluid communication with the first port, to receive a fraction of the exhaled breath collected in proportion to an instantaneous flow rate of the exhaled breath via the first port; and
    at least one sensor, in fluid communication with gas in the mixing chamber, to measure at least one of a volumetric flow rate, an oxygen content, a carbon dioxide content, an oxygen partial pressure, or a carbon dioxide partial pressure of the fraction of the exhaled breath.

2. The flow-rate proportional passive side-stream sampling system of claim 1, wherein the bend has a curve of about 75 degrees to about 105 degrees between the inlet and the outlet.

3. The flow-rate proportional passive side-stream sampling system of claim 1, wherein the bent flow tube has a second port disposed between the outlet of the bent flow tube and the bend, the second port in fluid communication with the mixing chamber and the inner lumen.

4. The flow-rate proportional passive side-stream sampling system of claim 1, further comprising:
    at least one valve, disposed between the inlet and the bend and in fluid communication with the inner lumen, to relieve pressure in the inner lumen during an inhalation by the person.

5. The flow-rate proportional passive side-stream sampling system of claim 1, further comprising:
    a saliva trap, disposed in fluid communication with the inner lumen, to collect saliva excreted by the person.

6. The flow-rate proportional passive side-stream sampling system of claim 1, further comprising:
a removable mouthpiece connected to the inlet of the bent flow tube.

7. The flow-rate proportional passive side stream sampling system of claim 1, wherein the mixing chamber further comprises a perforated baffle and/or a perforated circuit board disposed between the inlet and the at least one sensor to foster mixing of multiple breath fractions.

8. The flow-rate proportional passive side stream sampling system of claim 1, wherein the at least one sensor is disposed in the mixing chamber.

9. The flow-rate proportional passive side-stream sampling system of claim 1, wherein the bend substantially prevents the inhalation from flowing into the mixing chamber via the first port.

10. A method of proportional passive flow-rate sampling, the method comprising:
receiving an exhaled breath from a person at an inlet of a rigid bent flow tube;
conveying a fraction of the exhaled breath from a first port between the inlet of the rigid bent flow tube and a J-shaped bend in the rigid bent flow tube to a mixing chamber, the fraction of the exhaled breath being in proportion to an instantaneous flow rate of the exhaled breath; and
measuring, with at least one sensor, at least one of a volumetric flow rate, an oxygen content, a carbon dioxide content, an oxygen partial pressure, or a carbon dioxide partial pressure of the fraction of the exhaled breath.

11. The method of claim 10, wherein the J-shaped bend in the rigid bent flow tube is about 75 degrees to about 105 degrees between the inlet and the outlet, the rigid bent flow tube defining an inner lumen extending from a proximal end of the rigid bent flow tube to a distal end of the rigid bent flow tube to convey the exhaled breath from the proximal end to the distal end.

12. The method of claim 11, further comprising:
actuating at least one valve, disposed between the inlet and the J-shaped bend in the rigid bent flow tube, to relieve pressure in the inner lumen during an inhalation by the person.

13. The method of claim 10, wherein the rigid bent flow tube has a second port disposed between the J-shaped bend and an outlet of the rigid bent flow tube, and further comprising:
conveying gas from the mixing chamber to the second port; and
emitting the gas via the outlet.

14. The method of claim 10, further comprising:
collecting saliva excreted by the person with a saliva trap.

15. The method of claim 10, further comprising:
mixing fractions of multiple exhaled breaths in the mixing chamber.

16. A flow tube for a metabolic cart, the flow tube comprising:
a proximal end to receive an exhalation from a person;
a distal end;
a bend between the proximal end and the distal end;
a lumen extending from the proximal end to the distal end to convey the exhalation from the proximal end to the distal end;
a first port between the distal end and the bend, fluidically coupled to a mixing chamber and the lumen, to convey a portion of the exhalation from the mixing chamber to the lumen; and
a second port between the single bend and the proximal end, fluidically coupled to the mixing chamber and the lumen, to convey a portion of the exhalation to the mixing chamber from the lumen.

17. The flow tube of claim 16, wherein the bend is about 75 degrees to about 105 degrees.

18. The flow tube of claim 16, wherein the bend is about 90 degrees.

19. The flow tube of claim 16, further comprising:
at least one valve, disposed between the proximal end and the bend and in fluid communication with the lumen, to relieve pressure in the lumen during an inhalation by the person.

20. The flow tube of claim 16, further comprising:
a saliva trap, disposed in fluid communication with the lumen, to trap saliva excreted by the person.

21. The flow tube of claim 16, further comprising:
a removable mouthpiece inserted into the proximal end.

22. The flow tube of claim 16, wherein the flow tube has a length of about 7.75 inches to about 8 inches.

\* \* \* \* \*